United States Patent
Shio et al.

(10) Patent No.: US 6,511,668 B1
(45) Date of Patent: Jan. 28, 2003

(54) SILICON OXIDE POWDER AND PROCESS FOR MANUFACTURING THEREOF, AND COSMETIC PREPARATION, MICELLE HOLDING POWDER, AND PERFUME HOLDING POWDER, USING THE SAME

(76) Inventors: Shoichiro Shio, c/o Shiseido Recearch Center (1), 1050, Nippa-cho, Kohoku-ku, Yokohama-shi, Kanagawa 223-0057 (JP); Asa Kimura, c/o Shiseido Recearch Center (1), 1050, Nippa-cho, Kohoku-ku, Yokohama-shi, Kanagawa 223-0057 (JP)

(*) Notice: Subject to any disclaimer, the term of this patent is extended or adjusted under 35 U.S.C. 154(b) by 0 days.

(21) Appl. No.: 09/077,416
(22) PCT Filed: Sep. 30, 1997
(86) PCT No.: PCT/JP97/03487
§ 371 (c)(1),
(2), (4) Date: Nov. 23, 1998
(87) PCT Pub. No.: WO98/14399
PCT Pub. Date: Apr. 9, 1998

(30) Foreign Application Priority Data

Sep. 30, 1996 (JP) .............................. 8-278870
Feb. 18, 1997 (JP) .............................. 9-50965

(51) Int. Cl.[7] .......................... A61K 6/00; A61K 7/00; A61K 7/06; A61K 7/11; A61K 7/035
(52) U.S. Cl. ...................... 424/401; 424/69; 424/70.12
(58) Field of Search ................ 424/69, 70.12, 424/401

(56) References Cited

U.S. PATENT DOCUMENTS 5,057,296 A * 10/1991 Beck .......................... 423/277
5,599,759 A * 2/1997 Inagaki et al. ................ 502/80
5,849,258 A * 12/1998 Lujano et al. .............. 423/700
5,922,299 A * 7/1999 Bruinsma et al. ........... 423/335

FOREIGN PATENT DOCUMENTS

JP Hie 8-67578 3/1996 ........... C04B/38/06
JP wo98/14399 * 4/1998
WO WO 91/11390 A 8/1991

OTHER PUBLICATIONS

Chen, Cong–Yan et al., "Studies on mesoporous materials II. Synthesis mechanism of MCM–41", *Mesoporous Materials*, 1993, pp. 27–34, vol. 2, No. 1, Elsevier Science Publishers, Amsterdam, The Netherlands, (XP000576963).

Wang, Zichen et al., "Preparation of ultrafine $SiO_2$ with high surface area by the chemical precipitation method", *Materials Science & Engineering*, 1997, pp. 211–214, vol. B48, No. 3, Elsevier Science S.A., Lausane, Switzerland, (XP002125728).

Liu, J. et al., "Preparation of mesoporous Spherulites in Surfactant Solutions", *Journal of Porous Materials*, 1996, pp. 201–205, vol. 2, No. 3, Kluwer Academic Publishers, The Netherlands, (XP000863520).

Hong–Ping Lin, "Tubules–Within–A–Tubule" Hierarchical Order of Mesoporous Molecular Sieves in MCM–41, Science vol. 273, p. 765–767, Aug. 9, 1996.

* cited by examiner

Primary Examiner—Thurman K. Page
Assistant Examiner—S. Howard

(57) ABSTRACT

A non-laminar silicon oxide powder manufactured by a process comprising, a dissolution step wherein a concentration of 0.1–5.0M of a silicate which is in the range of $0<SiO_2/Y_2O<2$ (Y: alkali metal atom) is dissolved in the presence of a cationic surfactant and the pH is 11 or more, a condensation step wherein the pH is adjusted to 10.5 or less and a rod-like micelle is formed with said cationic surfactant and a silicate is condensed on said rod-like micelle, and a removal step wherein said cationic surfactant is removed from the micelle state condensation which has an outer shell made of the silicate by said condensation. The silicon oxide powder is useful as a carrier for cosmetics, pharmaceutical drugs and perfumes.

29 Claims, 15 Drawing Sheets

SILICON OXIDE POWDER AND PROCESS FOR MANUFACTURING THEREOF, AND COSMETIC PREPARATION, MICELLE HOLDING POWDER, AND PERFUME HOLDING POWDER, USING THE SAME

TECHNICAL FIELD

The present invention relates to a silicon oxide powder and a manufacturing process thereof and a cosmetic preparation, a micelle holding powder, and a perfume holding powder using the same and in particular, relates to an improvement of a shape of the powder.

BACKGROUND ART

A so-called mesoporous powder which has a mesopore of 2 to 50 nm pore size attracts attention as an adsorbent of gas or liquid, or as a carrier of a catalyst.

For example, a mesoporous powder which is disclosed in Japanese Unexamined Patent Publication No. Hei 8-67578, is composed of a three-dimensional structure which is made of a silicate and has a uniform pore of 1.5–10 nm in relative.

As for a manufacturing process of the mesoporous powder, a process for forming a three-dimensional structure by introducing a surfactant into an interlayer of a layer silicate such as kanemite and removing the surfactant with calcination or by removing a surfactant after gathering a silicate around the surfactant which was gathered in liquid with micelle state and the like are developed.

However, a particle size of the mesoporous powder is prescribed to the particle size of the layer silicate in the former process which uses the layer silicate. Also, since the mesoporous powder is laminar, it is feared that fluid resistance per pore degree is increased in the case where the mesoporous powder is used as a column packing.

On the contrary, though an examples which manufactured a rod-like porous powders are reported (Science Vol. 273 pp. 765–767), every rod-like porous powders has considerable large size. In particular, an external diameter is approximately 3 μm and a pore size becomes big far from mesoporous in the case where a pure silicic porous powder which is not contained aluminum. Therefore, a specific surface area becomes relatively small and there is a problem that the process is limited to use only for a molecular sceivetic use. Also, a rod-like mesoporous powder of certain fine particle size can be manufactured in the case where aluminum is contained in the powder. However, it is feared that catalytic activity becomes high due to the presence of aluminum. This process is also unfavorable.

DISCLOSURE OF INVENTION

In view of the above-mentioned problems of the prior art, a first object of the present invention is to provide a non-laminar silicon oxide powder which is comprised of silicon oxide in practical and has a fine diameter, and a process for manufacturing thereof.

Also, a second object of the present invention is to provide a micelle holding powder which efficiently holds a cationic material.

Further, a third object of the present invention is to provide a perfume holding powder that change of diffusion rate with time is small and that can holds a perfume through a long period of time.

As a result of diligent studies by the inventors for attaining the above-mentioned objects, it has been found that a fine diameter non-laminar silicon oxide powder can be obtained by reacting a silicate which has a specific ratio of silica/alkali metal under a specific concentration. Accordingly, the present invention has been accomplished.

Namely, a non-laminar silicon oxide powder in accordance with the present invention mainly composed of silicon oxide and has almost homogenous pore.

Also, in said powder, it is preferable that said powder is a fine mesoporous powder that a shape of said powder is fine shape and a depth of the pore is 50–300 nm.

Also, in said powder, it is preferable that said powder is a rod-like mesoporous powder that a shape of said powder is rod-like whose outer diameter is 20–200 nm and that a mesopore is elongated to its longer direction in the rod-like mesoporous powder.

Also, in said powder, it is preferable that said powder is a rod-like nonporous powder that a shape of said powder is rod-like whose diameter is 20–200 nm and the powder has no mesopore.

Also, in said powder, it is preferable that a primary particle is formed by aggregating two or more of rod-like substances in network state.

Also, a process for manufacturing a fine mesoporous powder in accordance with the present invention comprises a dissolution step wherein a concentration of 0.1–5.0M of a silicate which is in the range of 0<$SiO_2/Y_2O$<2 (Y: alkali metal atom) is dissolved in the presence of a cationic surfactant and the pH is 11 or more, a condensation step wherein the pH is adjusted to 10.5 or less, a rod-like micelle is formed with said cationic surfactant and a silicate is condensed on said rod-like micelle, and a removal step wherein said cationic surfactant is removed from a micelle state condensation which has an outer shell made of the silicate by said condensation.

Also, a process for manufacturing a rod-like mesoporous powder in accordance with the present invention comprises a dissolution step wherein a concentration of 0.3–1.2M of a silicate which is in the range of 0<$SiO_2/Y_2O$<2 (Y: alkali metal atom) is dissolved in the presence of a cationic surfactant and the pH is 11 or more, a condensation step wherein the pH is adjusted to 10.5 or less within 30 minutes, a rod-like micelle is formed with said cationic surfactant and a silicate is condensed on said rod-like micelle, and a removal step wherein said cationic surfactant is removed from a micelle state condensation which has an outer shell made of the silicate by said condensation.

Also, a process for manufacturing a rod-like nonporous powder in accordance with the present invention comprises a dissolution step wherein a concentration of 1.2–2.0M of a silicate which is in the range of 0<$SiO_2/Y_2O$<2 (Y: alkali metal atom) is dissolved in the presence of a cationic surfactant and the pH is 11 or more, a condensation step wherein the pH is adjusted to 10.5 or less within 30 minutes, a rod-like micelle is formed with said cationic surfactant and a silicate is condensed on said rod-like micelle, and a removal step wherein said cationic surfactant is removed from a micelle state condensation which has an outer shell made of the silicate by said condensation.

Also, in said manufacturing process, it is preferable that said silicate is mainly composed of $Na_2SiO_3$.

Also, in a process in accordance with the present invention, it is preferable that said cationic surfactant is a quaternary ammonium salt.

Also, in a process in accordance with the present invention, it is preferable that quaternary ammonium salt: silicate is 1:1–1:50 at molar ratio.

Also, in a process in accordance with the present invention, it is preferable that quaternary ammonium salt: silicate is 1:3–1:20 at molar ratio.

Also, in said process, it is preferable that said quaternary ammonium salt has an alkyl group having a carbon number of more than 18, in the case where a rod-like powder is formed.

Also, in said process, it is preferable that said quaternary ammonium salt has an alkyl group having a carbon number of 18 or less and coexist with 0.1–3M of an acid excluding silicon, in the case where a rod-like powder is formed.

Also, a cosmetic in accordance with the present invention comprises said non-laminar silicon oxide powder.

Also, a micelle holding powder in accordance with the present invention arranges silicate to a micelle outer shell of a cationic material which has surface active ability.

Also, in said micelle holding powder, it is preferable that said cationic material which forms micelle is a quaternary ammonium salt.

Also, in said micelle holding powder, said quaternary ammonium salt which forms micelle has antibacterial activity.

Also a process for manufacturing said micelle holding powder comprises a dissolution step wherein a silicate which is in the range of $0<SiO_2/Y_2O<2$ (Y: alkali metal atom) is dissolved in the presence of a cationic surfactant and the pH is more than pH 11, a condensation step that the pH is adjusted to 10.5 or less, a rod-like micelle is formed with said cationic surfactant and silicate is condensed on said rod-like micelle.

Also, a perfume holding powder in accordance with the present invention holds a perfume in said mesoporous powder.

BEST MODE FOR CARRYING OUT THE INVENTION

Figure 1:
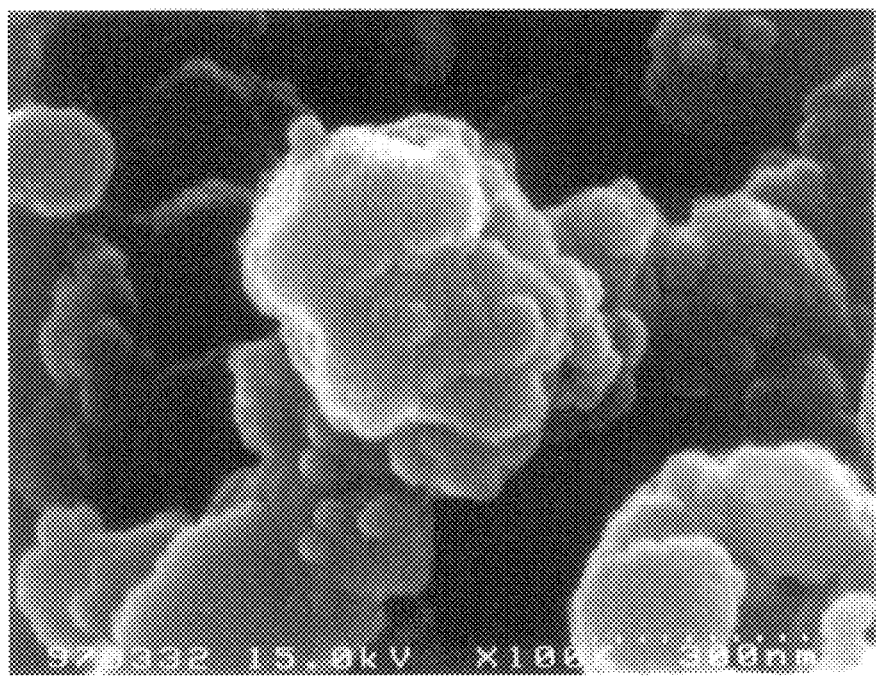
FIGS. 1–4 are explanatory views showing a relation between concentration of silicate and crystalline state.

The present inventors studied about behavior of a water-soluble component in the case where silicate is dissolved with alkali.

In the case where the present inventors further studied, it is cleared that silicate can be dissolved even in the presence of the surfactant by prescribing the range of the silicate within $0<SiO_2/Na_2O<2$ and a non-laminar silicon oxide powder which has extremely high homogeneity can be obtained by separating silicate ion which is in the dissolution state on the micelle of the quaternary ammonium salt.

Solubility of the silicate is deteriorated and the solution is clouded by adding the cationic surfactant in the case where said $SiO_2/Y_2O$ is more than 2. Also, homogeneity of the powder which is obtained in final is influenced by accumulating the silicate particles which are in insoluble state on the micelle.

On that respect, the solution is clouded due to the existence of the cationic surfactant and does not become favorable dissolution state and a homogenous mesoporous powder can not be obtained in the case where water-glass and the like which has more than 2 of $SiO_2/Y_2O$ are used as a raw material. As a technique for forming a mesoporous powder with the composition which has more than 2 of $SiO_2/Y_2O$, the technique which is disclosed in Japanese Unexamined Patent Publication No. Hei 5-503499 is existed. However, this is the technique for preparing a mesoporous powder which exists together with an aluminum compound in practical and there is no improvement about catalytic activity of the aluminum compound.

Also, a rod-like mesoporous powder or a rod-like non-porous powder can be prepared by prescribing the concentration of the silicate within the specific range.

The preferable embodiments of the present invention will be explained in the following.

Silicate

The silicates used in the present invention are $0<SiO_2/Y_2O<2$ (Y: alkali metal atom). As an examples of the alkali metal atom, in particular, Na or K is preferable in availability.

The above-mentioned silicate can be formed by reacting the various "materials which contains silicon" with the alkali such as NaOH.

As an examples of "materials which contains silicon", silicon oxide, silicate, silicon alkoxide, water-glass and the like are listed.

As an examples of the silicate, $Na_2SiO_3$, $Na_4SiO_4$ and the like are listed.

Also, as an examples of the silicon alkoxide, tetramethyl orthosilicate, tetraethyl orthosilicate, and the like are listed. It is preferable to use these materials together with e.g., silicate, because these materials has low reactivity in case of using separately.

Also, as an examples of the water-glass, JIS No.1, JIS No.2, JIS No.3 and the like are listed.

In this place, most of "materials which contains silicon" has more than 2.0 of $SiO_2/Na_2O$ and it is difficult to manufacture a homogenous non-laminar silicon oxide powder. Accordingly, the silicate which can be displayed as $0 < SiO_2/Na_2O < 2$ can be obtained by adding and dissolving e.g., an alkali agent such as sodium hydroxide. The silicate used in the present invention has no difficulty in forming a mesoporous powder in the case where $SiO_2/Na_2O$ is less than 0.5. However, the silicate is wasted in the case where an excess amount of the alkali agent is compounded. Also, the water solution is clouded and is difficult to become a complete dissolution state and is difficult to form a homogeneous silicon oxide powder in the case where $SiO_2/Na_2O$ is more than 2. Therefore, the silicate used in the present invention is preferably $0 < SiO_2/Y_2O < 2$, and more preferably is $0.5 \leq SiO_2/Na_2O \leq 1.9$.

Cationic Surfactant

As an examples of a cationic surfactant, a quaternary ammonium salt is preferable.

As for the quaternary ammonium salt, an alkyl quaternary ammonium salt $[R_4N]X$ and a cyclic quaternary ammonium salt,

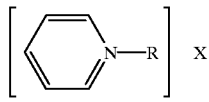

wherein in said quaternary ammonium salt, the quaternary ammonium salts which has a structure such as R: H, an alkyl group, an allyl group, a benzyl group, a phenyl group, a hydroxyl group and a hydroxyalkoxyl group, and X: $Cl^-$, $Br^-$, $I^-$ and $NO_3^-$, are listed.

These quaternary ammonium salts are required to form a rod-like micelle by adjusting the pH to 10.5 or less in the water solution.

In the case where R of the quaternary ammonium salt is the alkyl group having a carbon number more than 18, the rod-like powder is ready to be formed.

Also, in the case where R of the quaternary ammonium salt is the alkyl group having a carbon number of 18 or less, it is preferable to be existed with 0.1–3 M of acid residue excluding silicon, e.g., salts of $Cl^-$, $Br^-$ and $I^-$ in view of forming the rod-like powder.

Also, a process for manufacturing a mesoporous powder which is characterized in the present invention is constructed as follows.

Dissolution Step

The silicate and the cationic surfactant were mixed and the mixture was heated to room temperature or the temperature that both were dissolved. In the case where the pH in the time of the mixture was less than 11 or $SiO_2/Na_2O$ was equal to or more than 2, the pH was adjusted to 11 or more and $SiO_2/Na_2O$ was adjusted to less than 2 by adding the alkali agent.

A retention time required in this reaction may be relative short period which is required to rise up to the temperature that both ingredients are dissolved.

A ratio of the cationic surfactant with respect to the silicate is preferably 0.02–1.0, and more preferably is 0.05–0.3 at molar ratio. An amount of a rod-like micelle of the cationic surfactant is small in the case where the ratio of the cationic surfactant to the silicate is less than 0.02 at molar ratio. Also, a large amount of the unreacted cationic surfactant is remained in the case where the ratio of the cationic surfactant to the silicate is more than 1.0 at molar ratio. Both cases will be wasted.

Condensation Step

An acid was added to the solution which was obtained in said dissolution step in order to adjust the pH to 10.5 or less.

As a result, a rod-like micelle was formed by gathering the cationic surfactant or its globular micelle. Also, silicate ion which was in dissolved state at a pH of 11 or more, was condensed at the pH of 10.5 or less, and the silicate was arranged around the outer periphery of the rod-like micelle of the cationic acid. The powder which has an arrangement of hexagonal structure can be formed by this manipulation. The above-mentioned effects are not displayed sufficiently in the case where the pH is more than 10.5.

Removal Step

The dispersion that said powder was separated, was filtrated. Then, the cationic surfactant was removed. Water-washing and calcination are listed as an examples of this removal operation. The cationic surfactant was removed by this removal operation and thus a mesoporous powder can be obtained.

Study of $SiO_2/Y_2O$

First, a study about $SiO_2/Y_2O$ which is characterized in the present invention was conducted.

Namely, a proper amount of sodium hydroxide (manufactured by Nacalai Tesque Co., Ltd.) of a guaranteed reagent was dissolved into 1 liter of ion-exchanged water. 300 g of silicon dioxide (#200, manufactured by Aerosil Co. Ltd) which is commercially available was added to the dissolution and was stirred. Sodium silicate was obtained by calcining the dispersion for 5 hours at 700° C.

Then, the present inventors prepared sodium silicate which has various types of $SiO_2/Na_2O$ which are shown in TABLE 1 and tried to manufacture a mesoporous powder using these sodium silicates as a raw material.

TABLE 1

| $SiO_2/Na_2O$ | 0.5 | 1.0 | 1.5 | 2.0 |
|---|---|---|---|---|
| pH | 12.05 | 11.95 | 11.65 | 11.35 |
| Dissolution state | Completely dissolved | Completely dissolved | Completely dissolved | Semi-transparent |
| Specific surface area ($m^2/g$) | 1066 | 1126 | 1142 | 1052 |

A measurement of X-ray diffraction was also conducted at the same time. This measurement was conducted by using JDX-350 manufactured by JEOL Ltd., at 2 degree (2 θ)/min. CuK α ray was used as an X-ray source. Slit breadth was 1 degree-0.2mm-1 degree.

As a result of this experiment, it was confirmed from the result of X-ray diffraction that a hexagonal structure was formed in the case where sodium silicate was in dissolution state. However, a homogenous silicon oxide powder was sometimes not be obtained in the case where sodium silicate was not completely dissolved.

As is clear from the TABLE shown above, $SiO_2/Na_2O$ is preferably less than 2.0. Accordingly, it is understood that an appropriate powder can not be manufactured in this point, when water-glass and the like which are more than 2.0 of $SiO_2/Na_2O$ are directly used.

Also, in the case where $SiO_2/Na_2O$ was 2, sodium silicate sometimes could not be dissolved and a hexagonal structure was not formed. And, about 1.9 of $SiO_2/Na_2O$ is preferable in particular to form the hexagonal structure in stable.

Concentration of Silicate

It is preferable to adjust a concentration of silicate to form silicon oxide powder with rod-like state in the present invention.

Namely, a prescribed mol of sodium metasilicate and behenyltrimethylammonium chloride (BTC) were dissolved into 1 liter of ion-exchanged water. The temperature at this time was maintained at 70° C. The pH value of the mixture was adjusted to 8–9 with 2N hydrochloric acid solution just after the dissolution. Then, the dissolution was filtrated and washed with water. A powder was obtained by calcining the dissolution for 3 hours at 700° C.

TABLE 2

Figure 2:
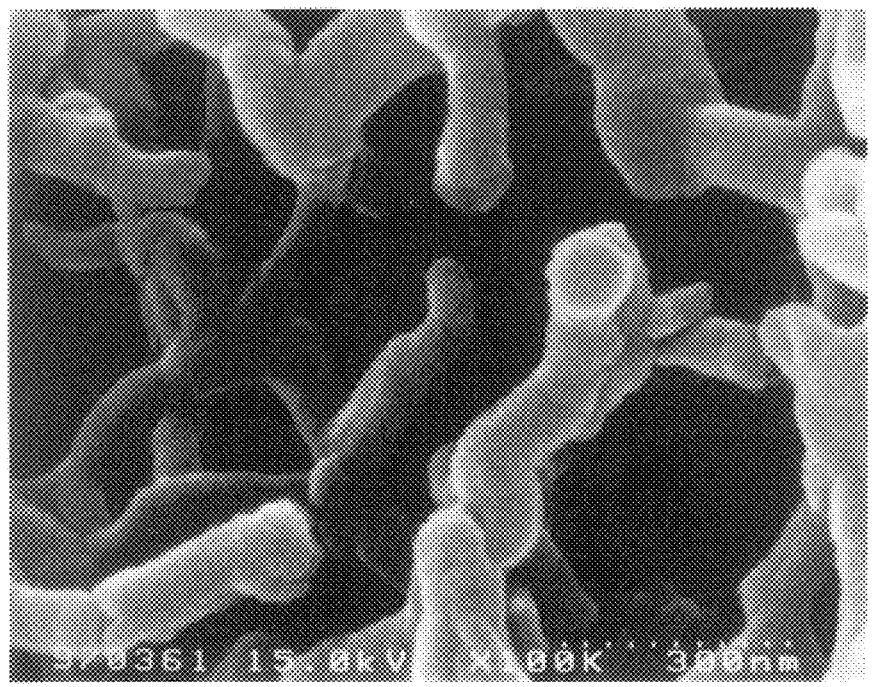
Figure 3:
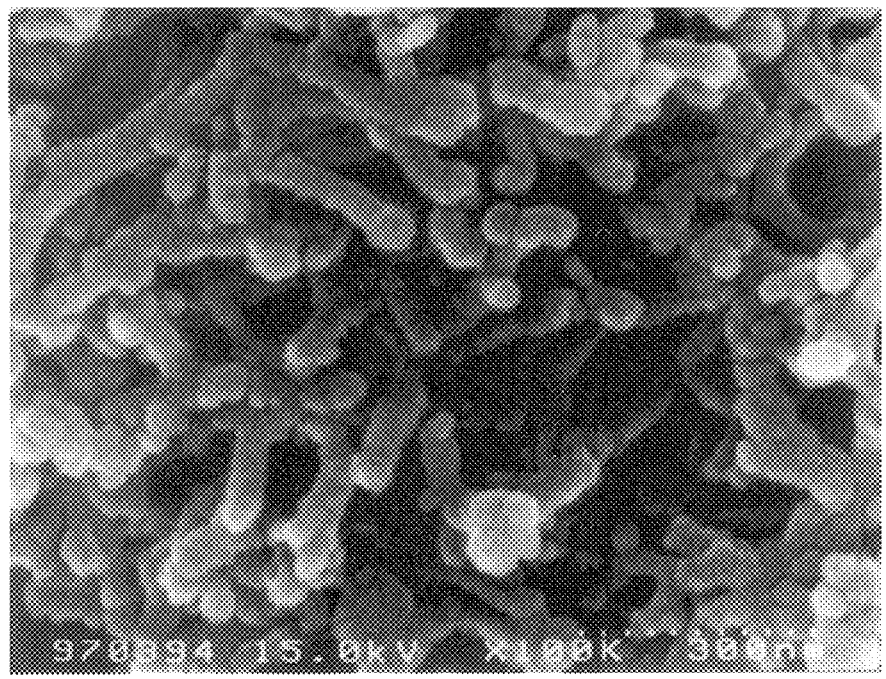
Figure 4:
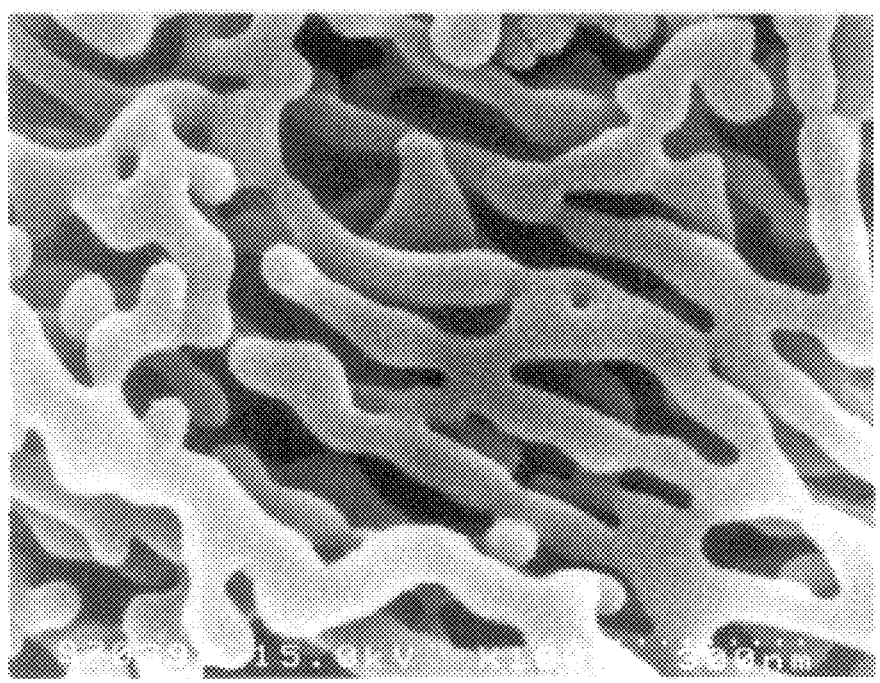

| Concentration of metasilicate (M) | 0.15 | 0.5 | 1.0 | 1.5 |
|---|---|---|---|---|
| BTC (M) | 0.03 | 0.1 | 0.2 | 0.3 |
| Property | Fine mesoporous FIG. 1 | Rod-like mesoporous FIG. 2 | Rod-like mesoporous FIG. 3 | Rod-like nonporous FIG. 4 |

As is clear from the result, the powder was mesoporous in the case where the concentration of the silicate was 0.15M, but the powder nevertheless became fine. Also, though the powder was rod-like in the case where the concentration of the silicate was 1.5M, there was almost no pore.

Then, it is possible to prepare a fine mesoporous powder in the case where the concentration of the silicate is 0.1M or more by the experiment of the inventors. Further, it was confirmed that a rod-like mesoporous powder was obtained with the concentration of 0.3 to 1.2M and a rod-like non-porous powder was obtained with the concentration of 1.2M or more, by adjusting the pH changing rate which will be described in the following.

Acid Addition Rate for pH Adjustment

It is preferable to adjust the addition rate of the acid for pH adjustment which was added at said condensation step in order that the powder can be formed with rod-like-state in the present invention.

Namely, 0.5 mol of sodium metasilicate and 0.1 mol of behenyltrimethylammonium chloride (BTC) were dissolved into 1 liter of ion-exchanged water as like the above, The temperature at this time was maintained at 70° C. The pH value of the mixture was adjusted to 8–9 with 2N hydrochloric acid solution just after the dissolution. The addition rate of 2N hydrochloric acid at this time was changed. Then, the dissolution was filtrated and washed with water. A powder was obtained by calcining the dissolution for 3 hours at 700° C.

TABLE 3

Figure 5:
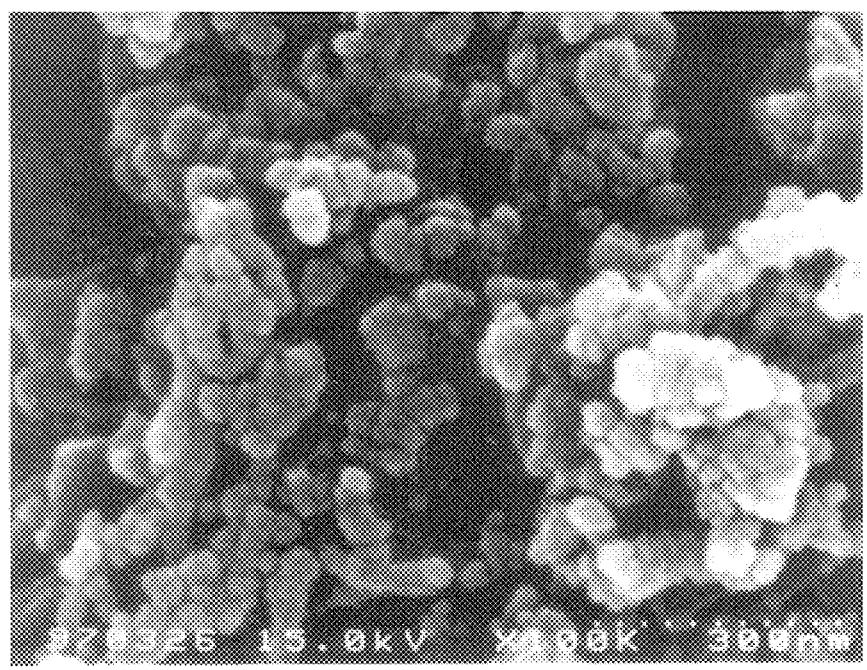
FIG. 5 is an explanatory view showing a relation between addition rate of acid for pH control and crystalline state.

| Addition rate of hydrochloric acid | 2 ml/min | 120 ml/min |
|---|---|---|
| Time required for pH adjustment | 150 min | 2.5 min |
| Property | Fine mesoporous FIG. 5 | Rod-like mesoporous FIG. 2 |

As is clear from the result, the powder became fine mesoporous in the case where the addition rate of 2N-hydrochloric acid was 2 ml/min. Also, the powder became rod-like mesoporous in the case where the addition rate of 2N-hydrochloric acid was 120 ml/min.

As a result of the more detailed experiment, it is preferable that the addition rate of hydrochloric acid was 10 ml/min or more (30 min or less for the necessary time of pH adjustment), in said condition.

Acid Concentration of pH Adjustment

It is preferable to adjust the concentration of the acid for pH adjustment which was added in said condensation step so as that the powder can be formed in rod-like state in the present invention.

Namely, 0.5 mol of sodium metasilicate and 0.1 mol of behenyltrimethylammonium chloride (BTC) were dissolved into 1 liter of ion-exchanged water, as like the above. The temperature at this time was maintained at 70° C. The pH value of the mixture was adjusted to 8–9 with the various concentrations of the hydrochloric acid solution with 120 ml/min just after the dissolution. Then, the dissolution was filtrated and washed with water. A powder was obtained by calcining the dissolution for 3 hours at 700° C.

TABLE 4

Figure 6:
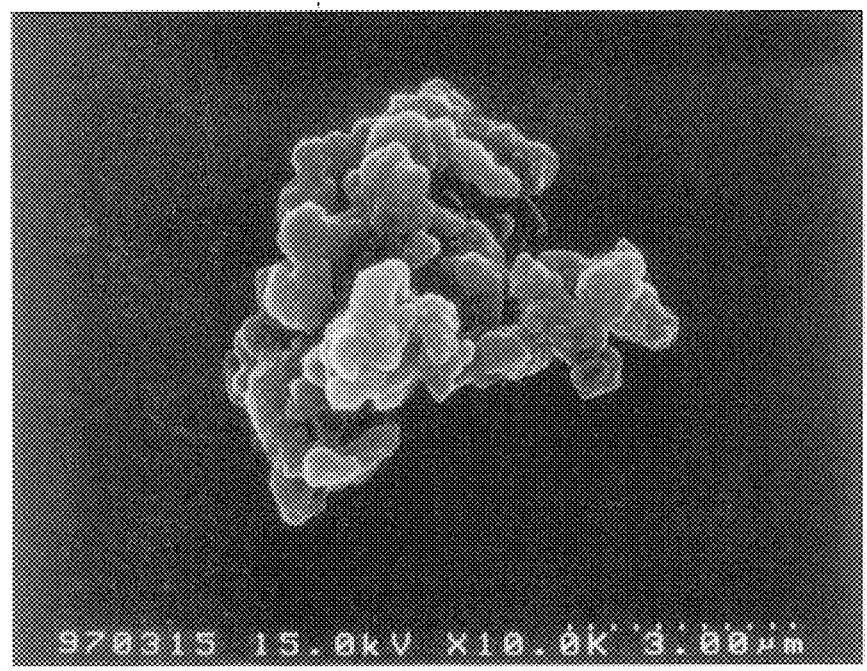
FIGS. 6 and 7 are an explanatory views showing a relation between concentration of acid for pH control and crystalline state.
Figure 7:
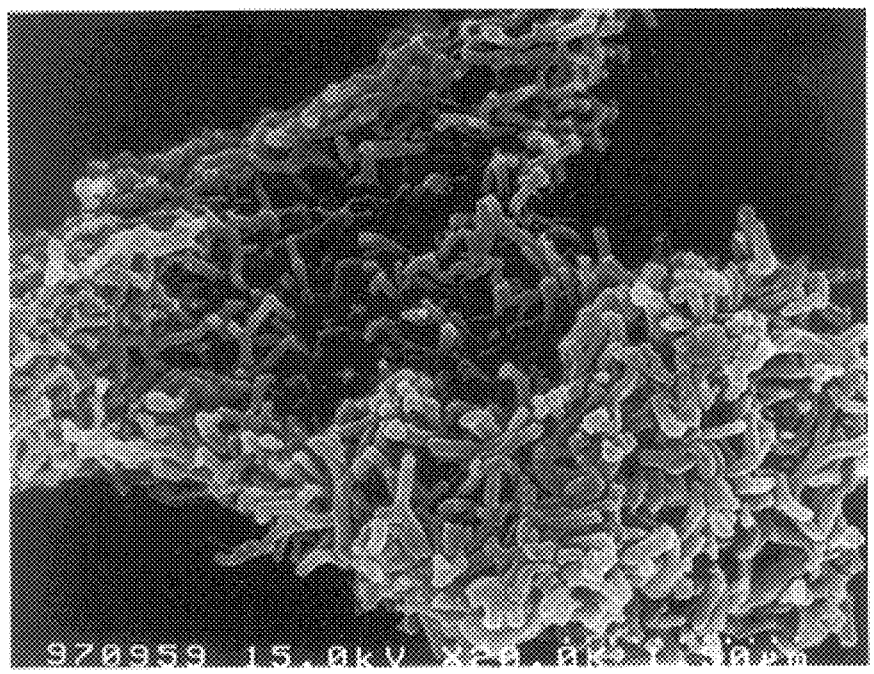

| Addition rate of hydrochloric acid | 0.2 N | 2 N | 5 N |
|---|---|---|---|
| Time required for pH adjustment | 35 min | 2.5 min | 1 min |
| Property | Fine mesoporous FIG. 6 | Rod-like mesoporous FIG. 2 | Rod-like mesoporous FIG. 7 |

As is clear from the result, the powder was mesoporous in the case where 0.2N-hydrochloric acid was used, but the powder became nevertheless fine. It is preferable that the concentration of hydrochloric acid is 2N or more for obtaining a rod-like mesoporous powder. However, though a rod-like mesoporous powder was obtained in the case where 5N-hydrochloric acid was used, the powder was slightly crumbled. Accordingly, the concentration of hydrochloric acid is preferably 1–5N, and more preferably is about 1.5–3N.

In consideration with the result regarding the above-stated acid addition rate, it can be thought that the necessary time of the pH changing rate is prescribed the difference to form rod-like or fine powder. In the case where the necessary time for pH adjustment at the time of sifting from the dissolution step to the condensation step was 30 minutes or more, the powder became fine. Also, in the case where the necessary time for pH adjustment was less than 30 minutes, the powder tended to became rod-like state.

The values of property in the case where the various powders were prepared with the same process, are shown in the following.

TABLE 5

|  | Fine mesoporous powder | Rod-like mesoporous powder | Rod-like nonporous powder |
|---|---|---|---|
| $Na_2SiO_3$ | 0.5 mol/L | 0.5 mol/L | 1.5 mol/L |
| Acid addition rate | 2 mL/min | 120 mL/min | 120 mL/min |
| Specific surface area | 1100 m²/g | 900 m²/g | 50 m²/g |
| Oil absorption | 300 mL/100 g | 500 mL/100 g | 400 mL/100 g |
| Size of pore | 30 Å | 35 Å | — |

As is clear from TABLE 5, it is understood that though a rod-like mesoporous powder has small specific surface area as compared with a fine mesoporous powder, the rod-like mesoporous powder has large oil absorption and excellent oil absorption property.

Also, said oil absorption was measured as shown in the following according to Japanese Industrial Standard (JIS).

Namely, 1–5 g of a sample was taken to a center of a measurement board. Squalane was gradually instilled onto the sample with 4–5 drops at a time from a burette and the whole part was sufficiently rubbed with a spatula in each time. When the whole part of the sample became a hard mass in patty-like with repeatedly dropping and rubbing, squalane was rubbed with every single drop. And this operation was terminated at the time that the sample could be a spiral shape by using a spatula.

A mesoporous powder in accordance with the present invention has a protection effect and a controlled release effect for an inner material because the mesoporous powder has a superb oil absorption property and a large pore. Also, the mesoporous powder is expected to apply for a pharmaceutical carrier and a column packing or cosmetics and foods.

Also, a rod-like powder aggregate in accordance with the present invention has not a pore, but it nevertheless has a large specific surface area. Consequently, tailing due to the pore is rarely occurred by using the rod-like powder aggregate as a column packing by introducing the various modified groups. Also, the rod-like powder aggregate can display a superb separability. Also, in the case where the rod-like powder aggregate was observed with per one particle, the rod-like powder aggregate had a structure which had a space in one particle because the rod-like powder was a network-state that a lot of rod-like were intertwined. Accordingly, the rod-like powder aggregate has, for example, an excellent oil and water absorption properties and is expected to apply for a pharmaceutical carrier or cosmetics, foods, and the like.

As is clear from TABLE 5, in the case where a mesoporous powder is observed as a column packing which classify a material by using a chemical affinity, the mesoporous powder which has 50 $m^2/g$ of an effective surface area which modified with a functional group is thought to be a favorable. Also, the mesoporous powder is expected that tailing is hardly occurred since the mesoporous powder does not have the pore. Further, though a specific surface area of the rod-like powder is smaller than that of the fine mesoporous powder, but the rod-like powder nevertheless has a large amount of oil absorption and a superb oil absorption properties. Also, in considering that chemical modification is easy to occur at an interface, though the specific surface area is small in relative, the rod-like powder nevertheless has a large amount of oil absorption. This indicates that the rod-like powder can hold a large amount of an oily component in stable.

Further it is preferable to conduct a hydrophobic or hydrophilic surface treatment according to, for example, an inner material or using environment.

A more definite examples of the present invention will be explained in the following.

Fine Mesoporous Powder

EXAMPLE 1-1

400 g of sodium hydroxide (manufactured by Nacalai Tesque Co., Ltd.) of a guaranteed reagent was dissolved into 1 liter of ion-exchanged water. 300 g of silicon dioxide (#200, manufactured by Aerosil Co. Ltd.) which is commercially available was added to the dissolution and was stirred. Sodium silicate ($NaSiO_3$) was obtained by calcining the dispersion for 5 hours at 700° C. 0.1 mol of said sodium silicate and 0.5 mol of stearyltrimethylammonium chloride were added to 1 liter of ion-exchanged water and were dissolved at 50° C. The pH value on this occasion was 11.8. Further, 2N-HCl was gradually added to the dissolution and the pH value was adjusted to 8.5. The dissolution was then filtrated and washed with water 5 times repeatedly and was dried by washing with acetone. A mesoporous powder was obtained by calcining this dry powder for 5 hours at 700° C.

EXAMPLE 1-2

0.5 mol of sodium metasilicate anhydride (manufactured by Nacalai Tesque Co., Ltd.) and 0.1 mol of stearyltrimethylammonium chloride were added to 1 liter of ion-exchanged water and were dissolved at 70° C. The pH value on this occasion was 11.75. Further, 2N-HCl was gradually added to the dissolution and the pH value was adjusted to 8.5. The dissolution was then filtrated and washed with water 5 times repeatedly and was dried by washing with acetone. A fine mesoporous powder was obtained by calcining this dry powder for 5 hours at 700° C.

Figure 8:
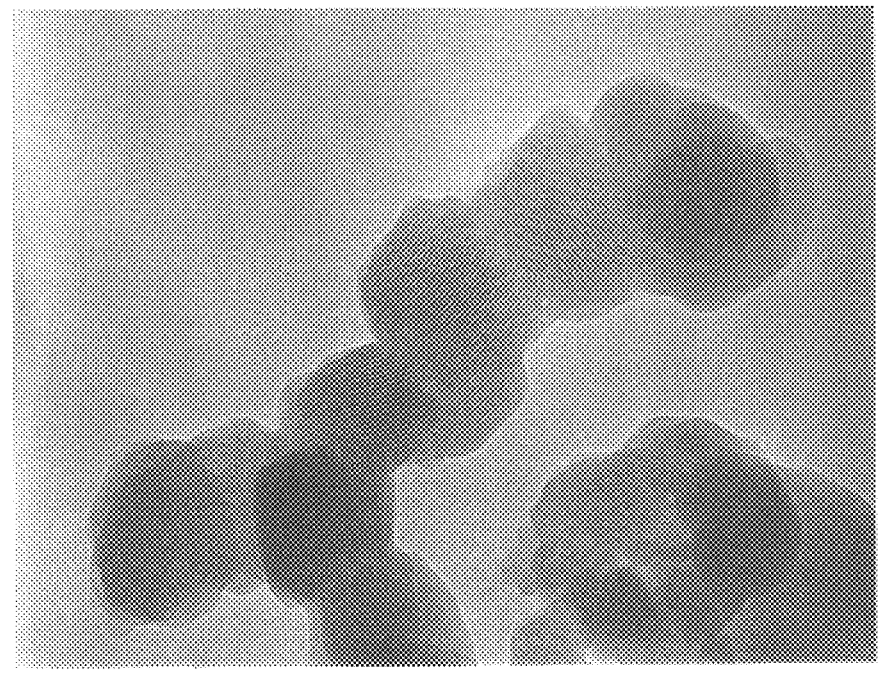
FIG. 8 is a TEM image showing a structure of a fine mesoporous powder in accordance with one embodiment of the present invention.

A TEM image of the fine mesoporous powder which was obtained by the above-mentioned process is shown in FIG. 8. In this drawing, some pores which elongates parallel in the powder are shown. When the fine mesoporous powder was observed as like above, a depth of the pore in this invention was 50–300 nm. And the depth of the pore is preferable in the view of releaser efficiency in case of holding a material.

EXAMPLE 1-3

30 g of sodium hydroxide (manufactured by Nacalai Tesque Co., Ltd.) of a guaranteed reagent was dissolved into 1 liter of ion-exchanged water. 30 g of silicon dioxide (#200, manufactured by Aerosil Co. Ltd.) which is commercially available was added to the dissolution and was stirred. 0.1 mol of stearyltrimethylammonium chloride was added to this dissolution and was dissolved at 70° C. The pH value on this occasion was 11.5. Further, 2N-HCl was gradually added to the dissolution and the pH value was adjusted to 8.5. The dissolution was then filtrated and washed with water 5 times repeatedly and was dried by washing with acetone. A fine mesoporous powder was obtained by calcining this dry powder for 5 hours at 700° C.

Figure 9:
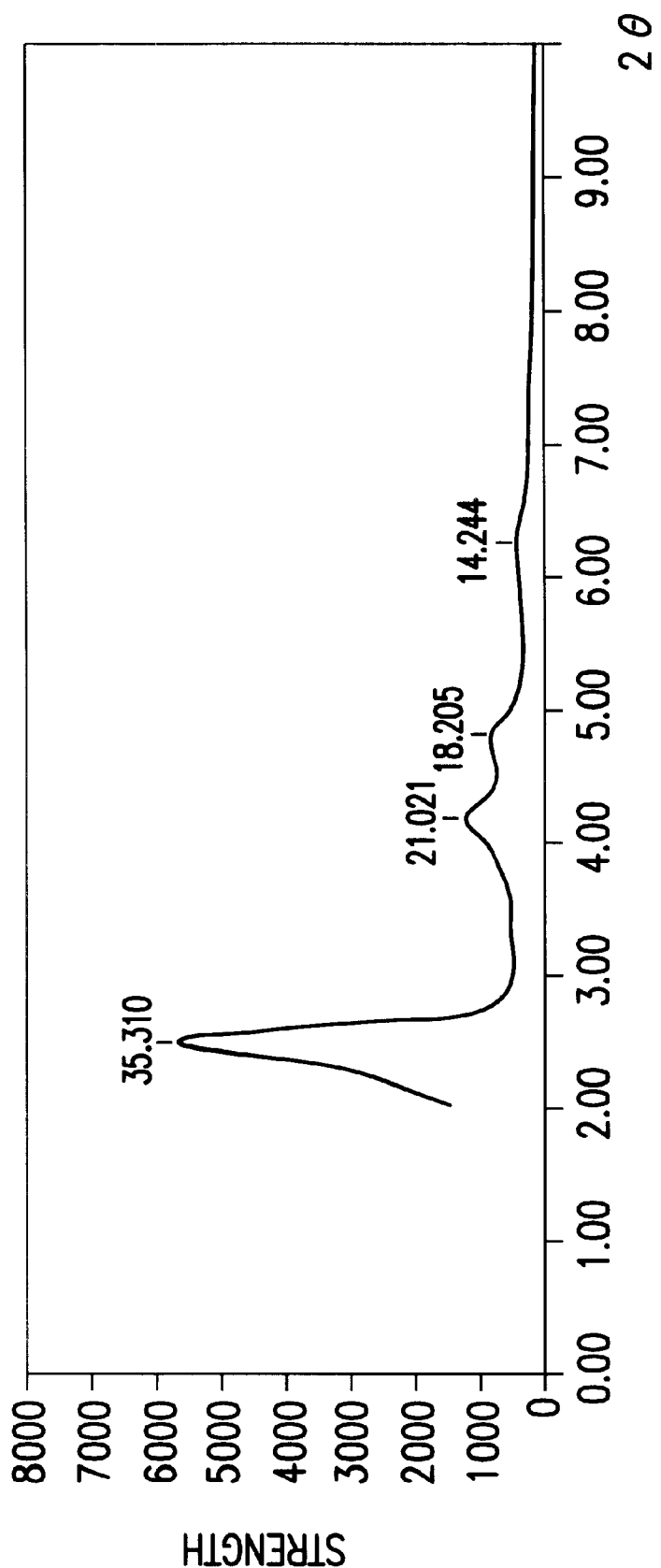
FIG. 9 is an X-ray diffraction diagram of a fine mesoporous powder which is obtained by the present invention.
Figure 10:
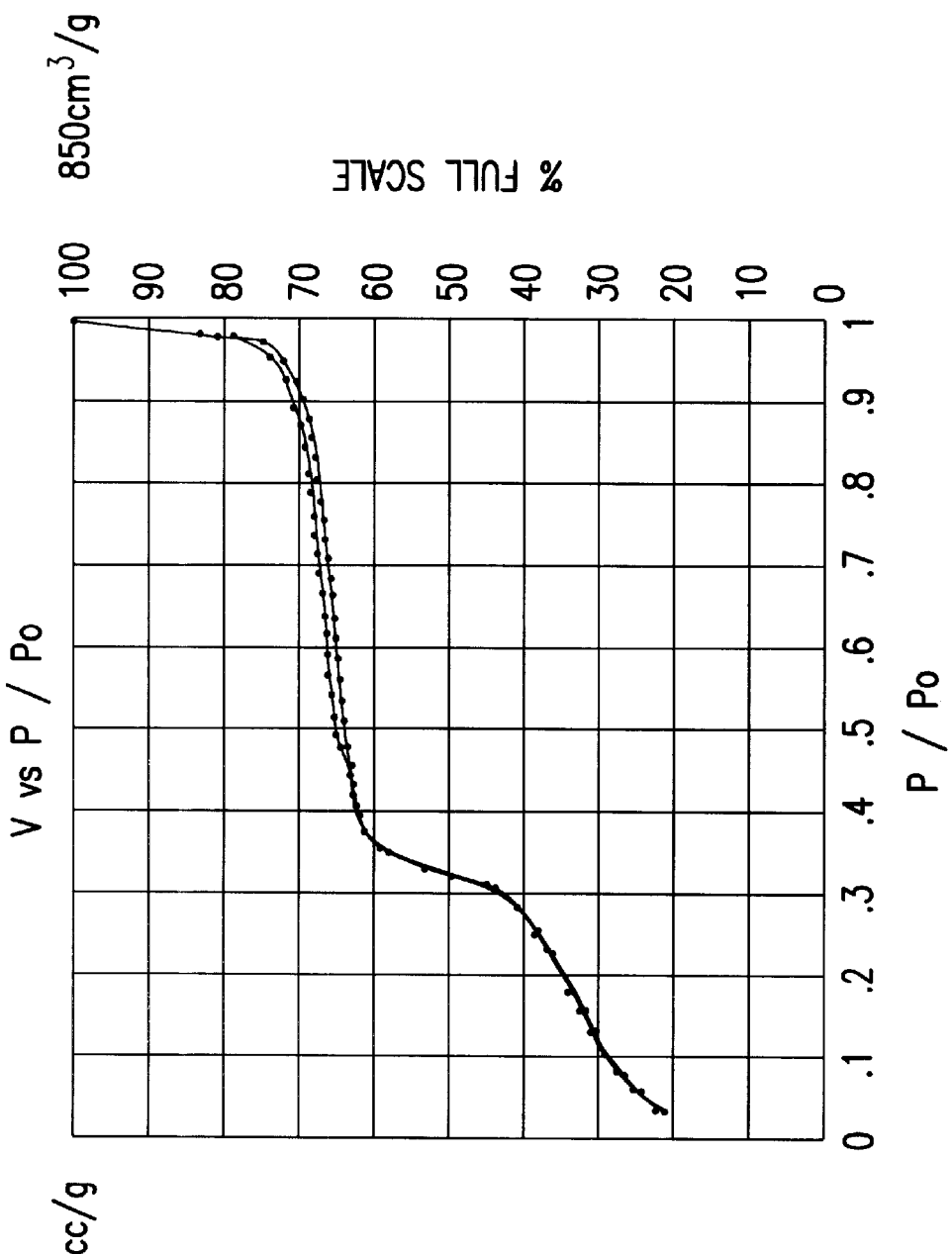
FIG. 10 is a nitrogen adsorption isotherm diagram of the fine mesoporous powder shown in FIG. 9.
Figure 11:
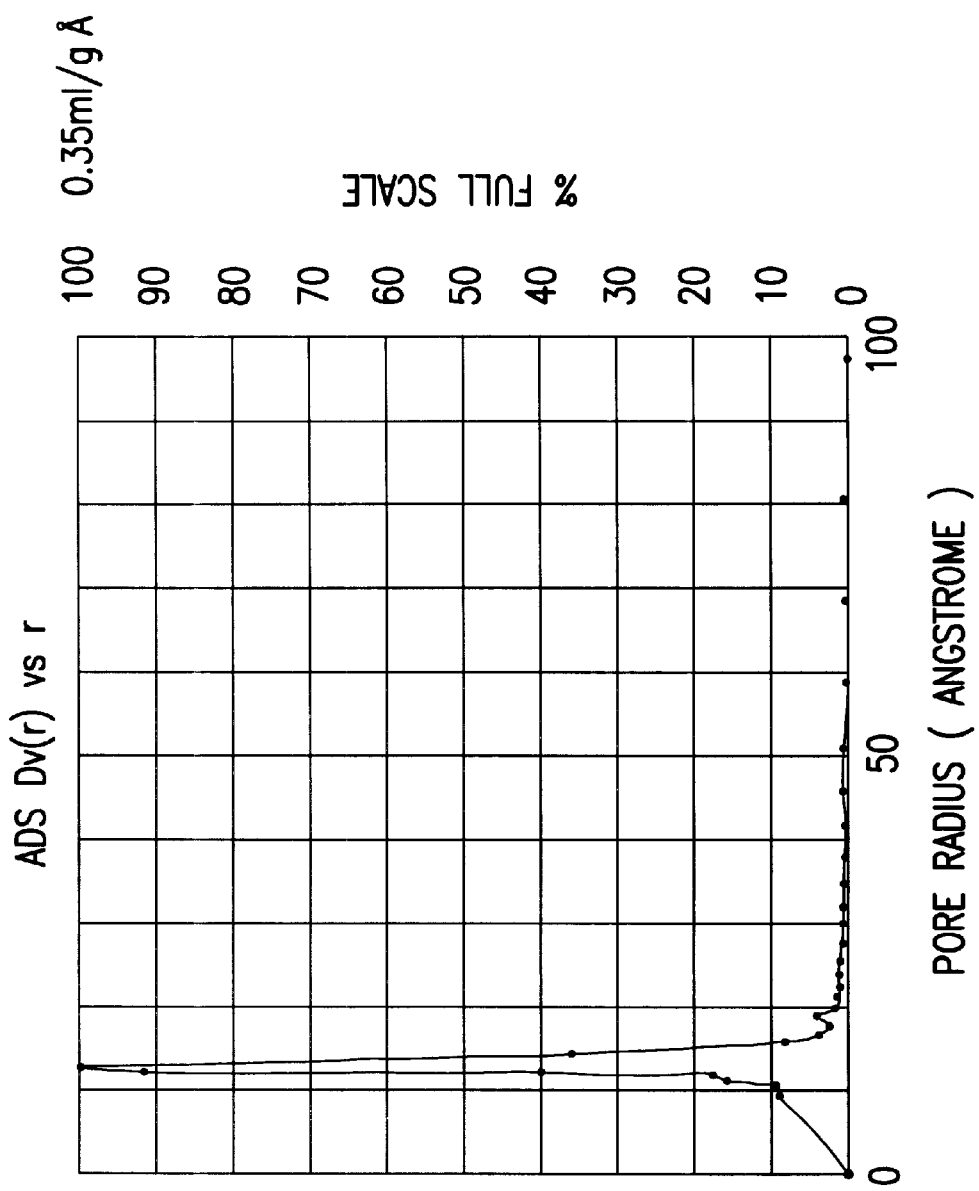
FIG. 11 is an explanatory view of a pore size distribution of the fine mesoporous powder shown in FIG. 9.

An X-ray diffraction diagram, a nitrogen adsorption isotherm and a pore size distribution which are obtained in this place are shown in FIG. 9, FIG. 10 and FIG. 11, respectively.

In here, the nitrogen adsorption isotherm was measured by using an autosorb automatic gas adsorption measurement apparatus sold from Yuasa Ionics according to B.E.T. method.

As shown in FIG. 9, diffraction strength shows four diffraction peaks which represents a hexagonal structure. Also, steep rising in the vicinity of relative vapor pressure (P/po)=0.35 of nitrogen adsorption isotherm which is shown in FIG. 10 represents the evenness of the pore size. More concretely, the evenness is clearly shown as the distribution of the pore size which was shown in FIG. 11.

Figure 12:
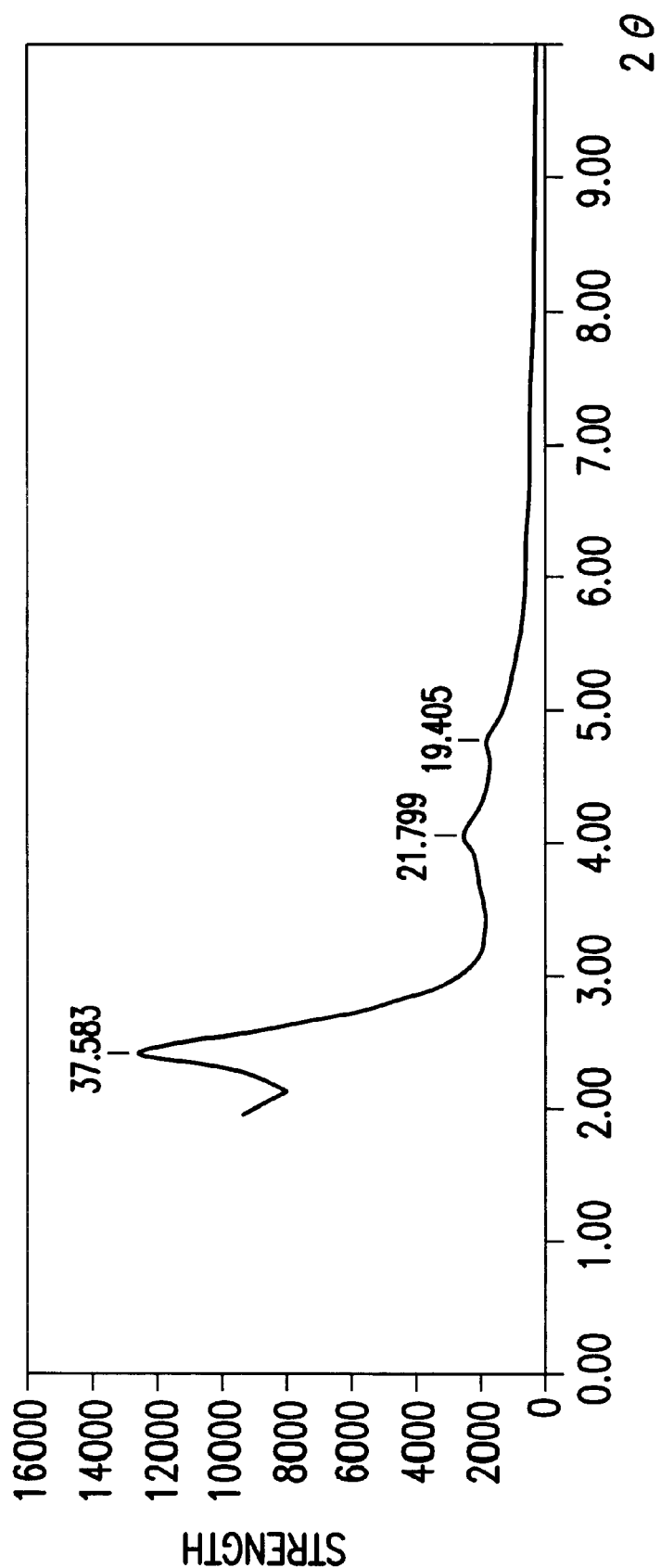
FIG. 12 is an X-ray diffraction diagram in the case where a fine mesoporous powder is manufactured by using KOH in the present invention.

Next, an X-ray diffraction diagram of the mesoporous powder which was manufactured as like the above-mentioned process except that the sodium hydroxide was substituted for potassium hydroxide with equimolar is shown in FIG. 12.

As is clear from FIG. 12, it is understood that the alkali excluding sodium hydroxide can be used for manufacturing a mesoporous powder of the present invention.

EXAMPLE 1-4

0.5 mol of sodium metasilicate anhydride (Nacalai Tesque) which is commercially available and 0.1 mol of cetyl trimethyl ammonium chloride were added to 1 liter of ion-exchanged water and were dissolved at 70° C. The pH value on this occasion was 11.84. Further, 2N-HCl was gradually added to the dissolution and the pH value was adjusted to 8.5. The dissolution was then filtrated and washed with water 5 times repeatedly and dried by washing with acetone. A fine mesoporous powder was obtained by calcining this dry powder for 5 hours at 700° C.

EXAMPLE 1-5

0.5 mol of sodium metasilicate anhydride (Nacalai Tesque) which is commercially available and 0.2 mol of lauryl trimethyl ammonium chloride were added to 1 liter of ion-exchanged water and were dissolved at 70° C. The pH value on this occasion was 11.92. Further, 2N-HCl was gradually added to the dissolution and the pH value was adjusted to 8.5. The dissolution was then filtrated and washed with water 5 times repeatedly and dried by washing with acetone. A fine mesoporous powder was obtained by calcining this dry powder for 5 hours at 700° C.

EXAMPLE 1-6

0.5 mol of sodium orthosilicate anhydride (Nacalai Tesque) which is commercially available, 0.1 mol of stearyl-trimethylammonium chloride and 0.1 mol of phenyl trimethyl ammonium chloride were added to 1 liter of ion-exchanged water and were dissolved at 70° C. The pH value on this occasion was 12.05. Further, 2N HCl was gradually added to the dissolution and the pH value was adjusted to 8.5. The dissolution was then filtrated and washed with water 5 times repeatedly and dried by washing with acetone. A fine mesoporous powder was obtained by calcining this dry powder for 5 hours at 700° C.

EXAMPLE 1-7

0.5 mol of stearyltrimethylammonium chloride was added to a mixture of 500 g of water glass ($SiO_2/Na_2O=2.0$) which is commercially available and 500 g of ion-exchanged water, and the mixture was dissolved at 70° C. The pH value on this occasion was 11.68. Further, 2N HCl was gradually added to the dissolution and the pH value was adjusted to 8.5. The dissolution was then filtrated and washed with water 5 times repeatedly and dried by washing with acetone. A fine mesoporous powder was obtained by calcining this dry powder for 5 hours at 700° C.

EXAMPLE 1-8

30 g of $SiO_2$ and 0.1 g of stearyltrimethylammonium chloride were dispersed and dissolved into 1 liter of ion-exchanged water. Then, 2 g of NaOH was added and dissolved into the. dispersion and the dispersion was stirred for 3 hours. The pH value on this occasion was 11.23. Further, 2N HCl was gradually added to the dissolution and the pH value was adjusted to 8.5. The dissolution was then filtrated and washed with water 5 times repeatedly and dried by washing with acetone. A fine mesoporous powder was obtained by calcining this dry powder for 5 hours at 700° C.

The properties of the mesoporous powders which were manufactured by the various examples described above are shown in TABLE 6.

TABLE 6

| | d100(Å) | ao(Å) | S.S.A($m^2$/g) | Total Pore Volume (cc) |
|---|---|---|---|---|
| Example 1–1 | 36.78 | 42.47 | 1125 | 2.06 |
| Example 1–2 | 38.38 | 44.32 | 1074 | 1.73 |
| Example 1–3 | 35.31 | 40.77 | 1210 | 1.84 |
| Example 1–4 | 34.62 | 39.98 | 1165 | 1.01 |
| Example 1–5 | 33.31 | 38.46 | 637 | 0.51 |
| Example 1–6 | 36.78 | 42.47 | 1077 | 2.32 |
| Example 1–7 | 37.56 | 43.37 | 1220 | 1.22 |
| Example 1–8 | 36.03 | 41.61 | 1242 | 1.01 |

Rod-like Mesoporous Powder

EXAMPLE 2-1

0.5 mol of sodium metasilicate ($Na_2SiO_3$) and 0.1 mol of behenyltrimethylammonium chloride (BTC) were dissolved into 1 liter of ion-exchanged water. The temperature at this time was maintained at 70° C. The pH value of the mixture was adjusted to 8–9 by adding 2N hydrochloric acid with flow velocity of 120 ml/min just after the dissolution. Then, the dissolution was filtrated and washed with water. A powder was obtained by calcining the dissolution for 3 hours at 700° C.

Figure 13:
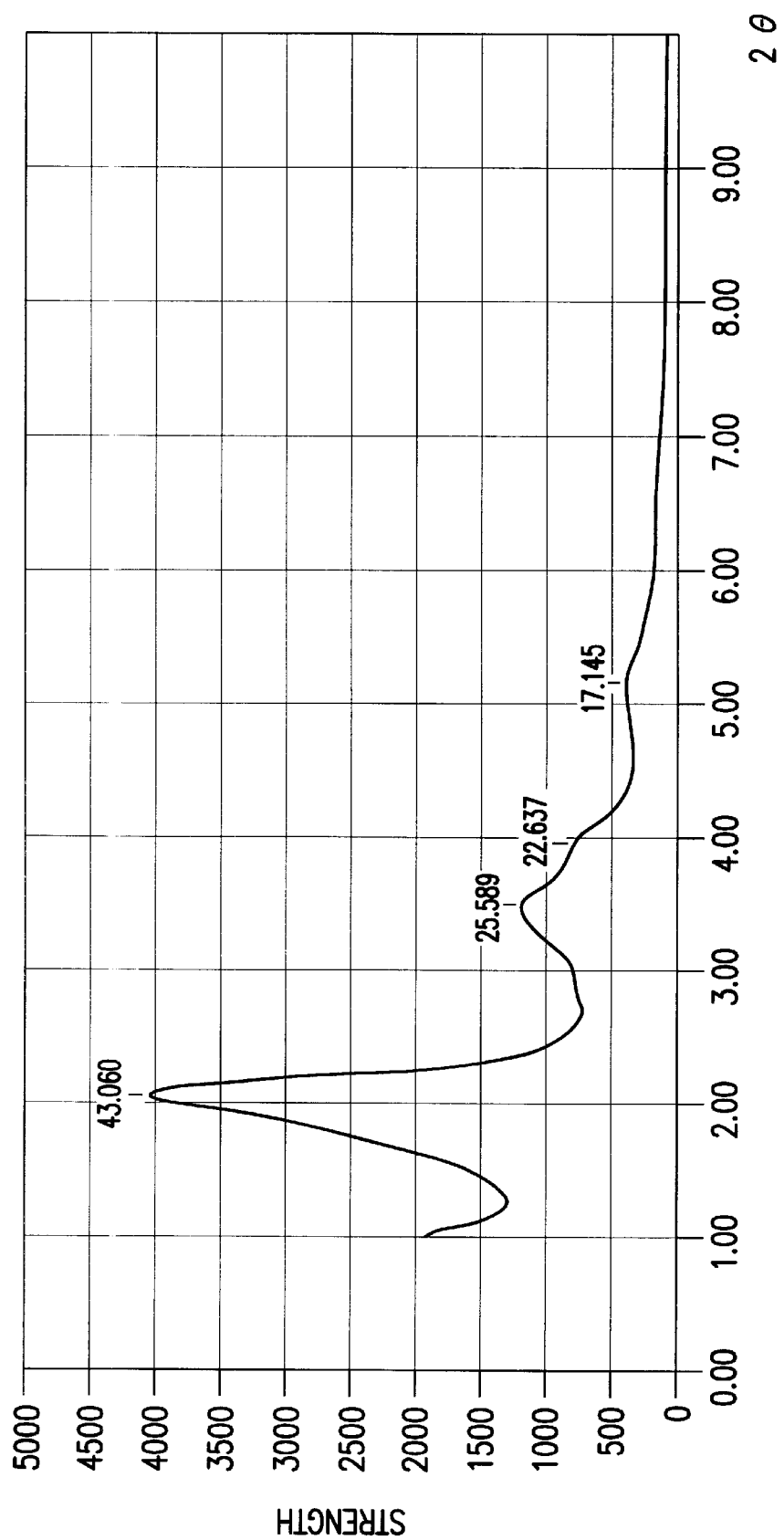
FIG. 13 is an X-ray diffraction diagram of a rod-like mesoporous powder which is obtained by the present invention.
Figure 14:
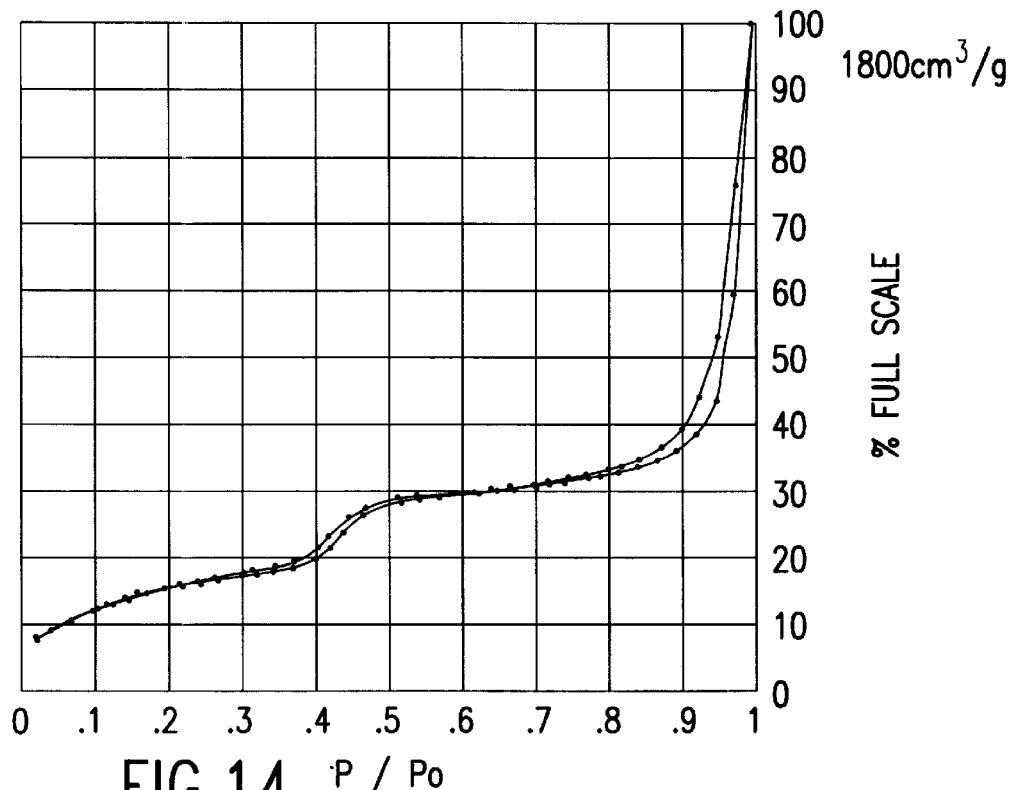
FIG. 14 is a nitrogen adsorption isotherm diagram of the rod-like mesoporous powder shown in FIG. 13.
Figure 15:
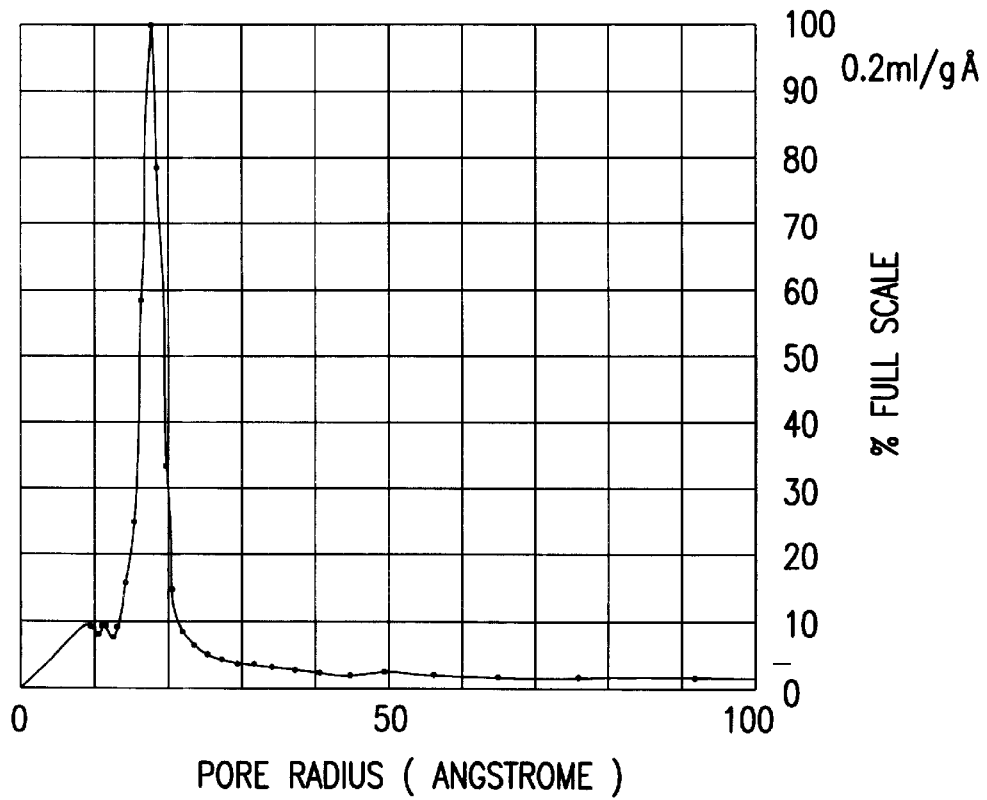
FIG. 15 is an explanatory view of a pore size distribution of the rod-like mesoporous powder shown in FIG. 13.

An X-ray diffraction diagram, a nitrogen adsorption isotherm and a pore size distribution which are obtained in this place are shown in FIG. 13, FIG. 14 and FIG. 15, respectively.

As shown in FIG. 13, diffraction strength shows four diffraction peaks which represents a hexagonal structure. Also, steep rising in the vicinity of relative vapor pressure (P/po)=0.45 of nitrogen adsorption isotherm which is shown in FIG. 14 represents the evenness of the pore size. More concretely, the evenness is clearly shown as the distribution of the pore size which was shown in FIG. 15.

EXAMPLE 2-2

0.5–1.2 mol of sodium metasilicate ($Na_2SiO_3$) and 0.05–0.24 mol of behenyltrimethylammonium chloride (BTC) were dissolved into 1 liter of ion-exchanged water. The temperature at this time was maintained at 70° C. The pH value of the mixture was adjusted to 8–9 by adding 2N-hydrochloric acid just after the dissolution. Then, the dissolution was filtrated and washed with water. A rod-like mesoporous powder was obtained by calcining the dissolution for 3 hours at 700° C.

In here, $Na_2SiO_3$/BTC was determined at 1/0.1–1/0.2. The rod-like mesoporous powder could be prepared when $Na_2SiO_3$/BTC was within this range.

EXAMPLE 2-3

0.5–1.2 mol of sodium metasilicate ($Na_2SiO_3$), 0.05–0.24 mol of stearyltrimethylammonium chloride (STC) and 0.5–2 mol of sodium chloride (NaCl) were dissolved into 1 liter of ion-exchanged water. After this, a rod-like mesoporous powder was obtained by the same process with Example 2-2.

In here, $Na_2SiO_3$/STC/NaCl was determined at 1/0.1/1–4 to 1/0.2/1–2. The rod-like mesoporous powder could be prepared when $Na_2SiO_3$/STC/NaCl was within this range.

EXAMPLE 2-4

0.5–1.2 mol of sodium metasilicate ($Na_2SiO_3$), 0.05–0.24 mol of stearyltrimethylammonium chloride (STC) and 0.5–2 mol of sodium bromide (NaBr) were dissolved into 1 liter of ion-exchanged water. After this, a rod-like mesoporous powder was obtained by the same process with Example 2-2.

In here, $Na_2SiO_3$/STC/NaBr was determined at 1/0.1/1–4 to 1/0.2/1–2. The rod-like mesoporous powder could be prepared when $Na_2SiO_3$/STC/NaBr was within this range.

EXAMPLE 2-5

0.5–1.2 mol of sodium orthosilicate ($Na_4SiO_4$) and 0.05–0.24 mol of behenyltrimethylammonium chloride (BTC) were dissolved into 1 liter of ion-exchanged water. After this, a rod-like mesoporous powder was obtained by the same process with Example 2-2.

In here, $Na_4SiO_4$/BTC was determined at 1/0.1–1/0.2. The rod-like mesoporous powder could be prepared when $Na_4SiO_4$/BTC was within this range.

EXAMPLE 2-6

0.5–1.2 mol of sodium metasilicate ($Na_2SiO_3$), 0.05–0.24 mol of behenyltrimethylammonium chloride (BTC) and 0–0.5 mol of silicon dioxide ($SiO_2$) were dissolved into 1 liter of ion-exchanged water. After this, a rod-like mesoporous powder was obtained by the same process with Example 2-2.

In here, $Na_2SiO_3+SiO_2$ was less than 1.3 mol. The rod-like mesoporous powder could be prepared when $Na_2SiO_3+SiO_2$ was within this range.

EXAMPLE 2-7

0.5–1.2 mol of sodium metasilicate ($Na_2SiO_3$), 0.05–0.24 mol of stearyltrimethylammonium bromide (STB) and 0.2–2 mol of sodium bromide (NaBr) were dissolved into 1 liter of ion-exchanged water. After this, a rod-like mesoporous powder was obtained by the same process with Example 2-2.

In here, $Na_2SiO_3$/STB/NaBr was determined at 1/0.1/1–4 to 1/0.2/1–2. The rod-like mesoporous powder could be prepared when $Na_2SiO_3$/STC/NaBr was within this range.

Rod-like Nonporous Powder

EXAMPLE 3-1

0.5 mol of sodium metasilicate ($Na_2SiO_3$) and 0.1 mol of behenyltrimethylammonium chloride (BTC) were dissolved into 1 liter of ion-exchanged water. The temperature at this time was maintained at 70° C. The pH value of the mixture was adjusted to 8–9 by adding 2N-hydrochloric acid with flow velocity of 120 ml/min just after the dissolution. Then, the dissolution was filtrated and washed with water. A rod-like nonporous powder was obtained by calcining the dissolution for 3 hours at 700° C.

Figure 16:
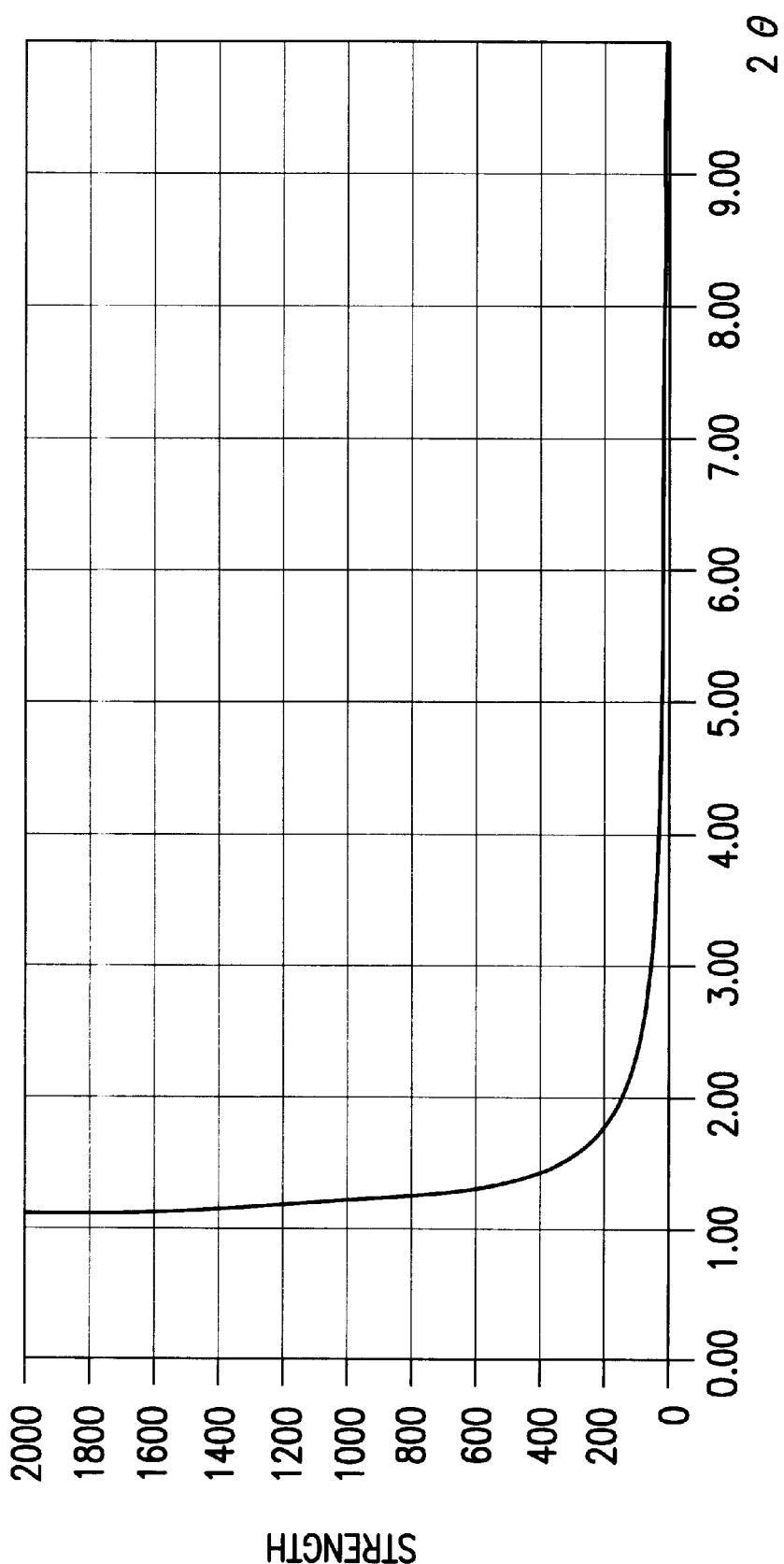
FIG. 16 is an X-ray diffraction diagram of a rod-like non-porous powder which is obtained by the present invention.
Figure 17:
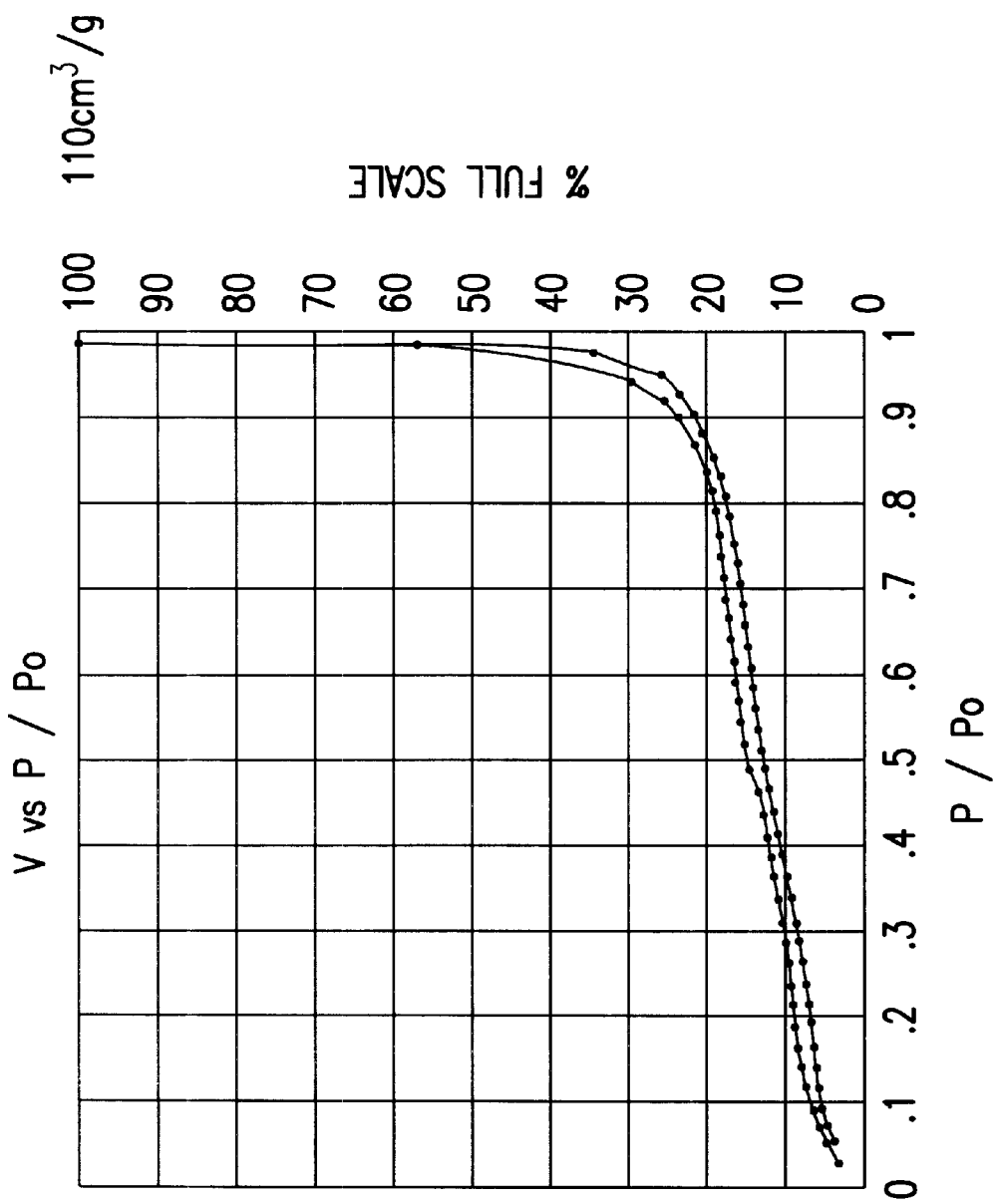
FIG. 17 is a nitrogen adsorption isotherm diagram of the rod-like nonporous powder shown in FIG. 11.

An X-ray diffraction diagram and a nitrogen adsorption isotherm are shown in FIG. 16 and FIG. 17, respectively.

As shown in FIG. 16, diffraction strength does not show any large diffraction peak. Also, consistency of the nitrogen adsorption isotherm shown in FIG. 17 shows that a pore does not exist practically.

EXAMPLE 3-2

1.3–2.0 mol of sodium metasilicate ($Na_2SiO_3$) and 0.13–0.2 mol of behenyltrimethylammonium chloride (BTC) were dissolved into 1 liter of ion-exchanged water. The temperature at this time was maintained at 70° C. The pH value of the mixture was adjusted to 8–9 by adding 2N-hydrochloric acid just after the dissolution. Then, the dissolution was filtrated and washed with water. A rod-like powder was obtained by calcining the dissolution for 3 hours at 700° C.

In here, $Na_2SiO_3$/BTC was determined at 1/0.1–1/0.2. The rod-like nonporous powder could be prepared when $Na_2SiO_3$/BTC was within this range.

EXAMPLE 3-3

1.3–2.0 mol of sodium metasilicate ($Na_2SiO_3$) and 0.13–0.2 mol of stearyltrimethylammonium chloride (STC) were dissolved into 1 liter of ion-exchanged water. After this, a rod-like powder was obtained by the same process with Example 3-2.

The rod-like powder could be prepared when $Na_2SiO_3$/STC was within this range.

EXAMPLE 3-4

1.2–2.0 mol of sodium metasilicate ($Na_2SiO_3$), 0.12–0.2 mol of stearyltrimethylammonium chloride (STC) and 0–1.5 mol of silicone dioxide ($SiO_2$) were dissolved into 1 liter of ion-exchanged water. After this, a rod-like nonporous powder was obtained by the same process with Example 3-2.

In here, $Na_2SiO_3+SiO_2$ was more than 1.2 mol. The rod-like nonporous powder could be prepared when $Na_2SiO_3+SiO_2$ was within this range.

Cosmetic Preparation

A silicon oxide powder which was manufactured according to the present invention has extremely high oil absorption as stated above and, for example, can improve a holding power on the skin because the powder can properly adsorb sebum in the case where the powder is compounded with an external preparation for skin such as cosmetics.

A compounding amount in the case where a silicon oxide powder is compounded to an external preparation for skin is at will according to a form of a cosmetic preparation and is 0.1–80 wt % in general.

The compounding amount of the silicon oxide powder in case of compounding to an emulsion or dispersion products is 0.1–50 wt % in general. Also, the compounding amount of the silicon oxide powder in case of compounding to a powder or pressed powder product, the compounding amount of the silicon oxide powder is 0.1–70 wt % in general.

Further, in addition to said silicon oxide powder, the other ingredients which generally compounded to an external preparation can be compounded within the qualitative and quantitative range that the effects of the present invention are not spoiled. For example, humectant, wax, pigment, oily component, surfactant, antiseptic, antioxidant, chelating agent, alkali, water-soluble high polymer, oil-soluble high polymer, clay mineral, and the like can be listed.

The present inventors prepared a powdery foundation as shown in TABLE 7 and verified the effects of said mesoporous powder.

TABLE 7

|  | Compounding Example 4-1 | Comparative Example 4-1 | Comparative Example 4-2 | Comparative Example 4-3 |
|---|---|---|---|---|
| Porous powder |  |  |  |  |
| Rod-like mesoporous powder | 5.0 |  |  |  |

TABLE 7-continued

|  | Compounding Example 4-1 | Comparative Example 4-1 | Comparative Example 4-2 | Comparative Example 4-3 |
|---|---|---|---|---|
| Silica gel |  | 5.0 |  |  |
| Zeolite |  |  | 5.0 |  |
| Normal powder |  |  |  |  |
| Talc | 10.0 | 10.0 | 10.0 | 15.0 |
| Mica | 52.95 | 52.95 | 52.95 | 52.95 |
| Yellow iron oxide | 1.0 | 1.0 | 1.0 | 1.0 |
| Red iron oxide | 0.5 | 0.5 | 0.5 | 0.5 |
| Black iron oxide | 0.05 | 0.05 | 0.05 | 0.05 |
| Titanium oxide | 5.0 | 5.0 | 5.0 | 5.0 |
| Oily component |  |  |  |  |
| Liquid petrolatum | 20.0 | 20.0 | 20.0 | 20.0 |
| Lanolin | 5.0 | 5.0 | 5.0 | 5.0 |
| Ethylparaben | 0.3 | 0.3 | 0.3 | 0.3 |
| Perfume | 0.2 | 0.2 | 0.2 | 0.2 |
| Effects |  |  |  |  |
| Sliding | ○ | Δ | Δ | ○ |
| Cosmetic durability | ○ | ○ | ○ | X |

Each powder was contained in a Henschel mixer and was stirred uniformly. The residuary ingredients were then added and mixed uniformly. The powdery foundation was obtained by grinding the mixture by an atomizer and forming at a medium-sized pan.

In consideration of TABLE 7, an improvement of cosmetic durability was observed in the case where a porous powder such as silica gel or zeolite (Comparative example 4-1, 2) was compounded, as compared with the case where the porous powder was not compounded (Comparative example 4-3). However, sufficient improvement was not displayed, since it had a problem in sliding in the case where the foundation was coated on the skin.

On the contrary, an improvements of usability and cosmetic durability were observed in the case where the mesoporous powder was compounded. This indicated a superior properties of the mesoporous powder.

Also, the same effects with this powder were observed in the case where a fine mesoporous powder and a rod-like nonporous powder were used.

Evaluation of Cosmetic Durability (Perspiration Resistance)

The above-mentioned external preparation for skin was applied to the faces of 20 female panels who were 20 to 29 years old. Then they read a book in a room for 2 hours. After self evaluation of cosmetic durability at the point of time, they were running 2 km in the open air. They evaluated the crumbling of cosmetic by themselves causing of the perspiration after running according to the following evaluation standard.

<Evaluation Standard>

◎: Number of the panel answered that cosmetic was spoiled is 0
○: Number of the panel answered that cosmetic was spoiled is 1–5
Δ: Number of the panel answered that cosmetic was spoiled is 6–11
X: Number of the panel answered that cosmetic was spoiled is 12 or more Next, the inventors further added methyl salicylate to the compositions of TABLE 8 and studied irritativeness of the compositions and persistence of the effect.

TABLE 8

|  | Compounding Example 4-2 | Comparative Example 4-4 | Comparative Example 4-5 | Comparative Example 4-6 |
|---|---|---|---|---|
| Porous powder |  |  |  |  |
| Rod-like mesoporous powder | 5.0 |  |  |  |
| Silica gel |  | 5.0 |  |  |
| Zeolite |  |  | 5.0 |  |
| Normal powder |  |  |  |  |
| Talc | 10.0 | 10.0 | 10.0 | 15.0 |
| Mica | 51.95 | 51.95 | 51.95 | 51.95 |
| Yellow iron oxide | 1.0 | 1.0 | 1.0 | 1.0 |
| Red iron oxide | 0.5 | 0.5 | 0.5 | 0.5 |
| Black iron oxide | 0.05 | 0.05 | 0.05 | 0.05 |
| Titanium oxide | 5.0 | 5.0 | 5.0 | 5.0 |
| Oily component |  |  |  |  |
| Liquid petrolatum | 20.0 | 20.0 | 20.0 | 20.0 |
| Lanolin | 5.0 | 5.0 | 5.0 | 5.0 |
| Ethylparaben | 0.3 | 0.3 | 0.3 | 0.3 |
| Methyl salicylate | 1.0 | 1.0 | 1.0 | 1.0 |
| Perfume | 0.2 | 0.2 | 0.2 | 0.2 |
| Effects |  |  |  |  |
| Skin irritation | ◎ | Δ | Δ | X |
| Durability of effect | ◎ | Δ | Δ | X |

Though methyl salicylate which was compounded in an oil phase was useful as a UV-absorber, it sometimes caused skin irritation in the case where a large amount of methyl salicylate was compounded. On the contrary, since a porous powder adsorbed methyl salicylate and methyl salicylate was gradually discharged by equilibrium relation between an outer phase, skin irritation at the beginning of application was lowered and persistence of its effect could be schemed in the case where the porous powder was compounded.

In consideration of TABLE 8, skin irritation of methyl salicylate can be lowered by a porous powder such as silica gel or zeolite. In particular, skin irritation due to methyl salicylate can be controlled in extremely favorable with the mesoporous powder. Further persistence of UV-absorption effect can be largely improved.

The same effects with this were observed in the case where a fine mesoporous powder was used.

Evaluation of the effects has done according to the following.

Namely, a sample which will be mentioned in the following was applied to upper arm of 25 each both sexes panel. Irritativeness such as sore feeling were evaluated after 30 minutes of application. Persistence of the effect after 3 hours was also evaluated. Each evaluation standard is shown as follows.

Skin Irritativeness

◎: 0–5 among 50 panels admitted sore feeling in the skin
○: 6–20 among 50 panels admitted sore feeling in the skin
Δ: 21–35 among 50 panels admitted sore feeling in the skin p1 X: 36–50 among 50 panels admitted sore feeling in the skin Persistence of Effect ◎: 36–50 among 50 panels admitted persistence feeling of the effect
○: 21–35 among 50 panels admitted persistence feeling of the effect
Δ: 6–20 among 50 panels admitted persistence feeling of the effect X: 0–5 among 50 panels admitted persistence feeling of the effect Next, the present inventors studied the relation between the mesoporous powder and its effect.

TABLE 9

| Compounding examples | 4-3 | 4-4 | 4-5 | 4-6 | 4-7 | 4-8 | 4-9 | 4-10 | 4-11 |
|---|---|---|---|---|---|---|---|---|---|
| Porous powder | | | | | | | | | |
| Rod-like mesoporous powder | 0.01 | 0.1 | 0.05 | 1.0 | 5.0 | 10.0 | 30.0 | 50.0 | 80.0 |
| Normal powder | | | | | | | | | |
| Talc | 34.99 | 34.9 | 34.5 | 34.0 | 30.0 | 25.0 | 5.0 | 0 | 0 |
| Mica | 46.95 | 46.95 | 46.95 | 46.95 | 46.95 | 46.95 | 46.95 | 31.95 | 1.95 |
| Yellow iron oxide | | | | 1.0 | | | | | |
| Red iron oxide | | | | 0.5 | | | | | |
| Black iron oxide | | | | 0.05 | | | | | |
| Titanium oxide | | | | 5.0 | | | | | |
| Oily component | | | | | | | | | |
| Liquid petrolatum | | | | 5.0 | | | | | |
| Lanolin | | | | 5.0 | | | | | |
| Ethylparaben | | | | 0.3 | | | | | |
| Methyl salicylate | | | | 1.0 | | | | | |
| Perfume | | | | 0.2 | | | | | |
| Effect | | | | | | | | | |
| Skin irritation | X | Δ | ○ | ◎ | ◎ | ◎ | ◎ | ◎ | ◎ |
| Durability of effect | X | ○ | ○ | ○ | ◎ | ◎ | ◎ | ◎ | ◎ |
| Roughness | ○ | ○ | ○ | ○ | ○ | ○ | ○ | ○ | Δ |

As is clear from TABLE 9, the effect by adding the mesoporous powder could be observed about 0.1% of the mesoporous powder. This effect became clear in the case where about 1.0% of the mesoporous powder was compounded. On the other hand, distinctive effect of the present invention could be displayed without any problems even in the case where the amount was raised to the considerable amount. However, 80 wt % of the mesoporous powder, though it depends on the particle size of the mesoporous powder, had a tendency to cause a slight roughness.

Accordingly, the compounding amount of the mesoporous powder is 0.1% or more, and more preferably is 1.0%–80 wt % in the external preparation for skin of the present invention.

A concrete compounding examples of the composition in accordance with the present invention will be explained in the following.

| Compounding Example 4-12 Lipstick | |
|---|---|
| Polyethylene wax | 3% |
| Ceresine wax | 10 |
| Carnauba wax | 2 |
| Candelilla wax | 5 |
| Liquid petrolatum | 30 |
| Castor oil | 15 |
| Di-2-glyceryl heptyl undecanoic acid | 20 |
| Olive Oil | 11 |
| Red iron oxide | 0.2 |
| Red No. 202 | 1.8 |
| Silicon oxide powder | 2 |

<Manufacturing Process>

The oily components and wax were heated and dissolved at 85–90° C. The pigments were added to the dissolution and dispersed. Then, the dispersion was immediately vacuum deaerated and was transferred to the prescribed container. A lipstick was obtained by cooling and solidifying it.

Thus obtained lipstick was difficult to remove after application.

| Compounding Example 4-13 Pressed-State Eye Shadow | |
|---|---|
| Talc | 26 |
| Mica | 35 |
| Titanium coated mica | 20 |
| Liquid petrolatum | 2.8 |
| Dimethyl polysiloxane (6 cs) | 2 |
| Silicon oxide powder | 5 |
| Sorbitan monooleate | 1 |
| Ultramarine | 8 |
| Red No. 201 | 0.2 |

<Manufacturing Process>

After mixing the powders excluding titanium coated mica by a Henschel mixer, the oily components and the surfactant were added to the mixture and ground by a pulverizer. Titanium coated mica was further added to the mixture and mixed uniformly by a Henschel mixer. An eye shadow was obtained by compression molding the mixture to the prescribed medium-sized pan.

| Compounding Example 4-14 Baby Powder | |
|---|---|
| Silicon oxide powder | 40 |
| Talc | 58.7 |
| Citric acid | 0.2 |
| Red iron oxide | 0.01 |
| Liquid petrolatum | 1 |
| Perfume | 0.09 |

<Manufacturing Process>

Citric acid was dissolved by 99% alcohol. The dissolution was added to talc and mixed by a Henschel mixer. Then, alcohol was removed at 80° C. The residual were added to the mixture and ground by an atomizer. A baby powder was obtained by directly transferring to the prescribed container.

Compounding Example 15
Emulsion Foundation

| | |
|---|---|
| Stearic acid | 0.7 |
| Isopropyl myristate | 4 |
| Squalane | 22 |
| Polyoxyethylene (10 mol) stearyl ether | 2 |
| Cetyl alcohol | 0.3 |
| Talc | 7 |
| Silicon oxide powder | 3 |
| Iron oxide pigment | 2.5 |
| Red No. 202 | 0.5 |
| Antiseptic | 0.09 |
| Triethanolamine | 0.42 |
| Propylene glycol | 5 |
| Purified water | 52.19 |
| Perfume | 0.3 |

<Manufacturing Process>

After heating, mixing and dissolving the oily components and surfactant, the pigments were added and dispersed to the dissolution uniformly. A dissolution that triethanolamine and propylene glycol were dissolved into purified water and were heated was added to the dispersion and was emulsified. The emulsion was cooled down with stirring and was uniformed by adding perfume. An emulsion foundation was obtained by filling the emulsion to a container.

Compounding Example 4-16
Rouge

| | |
|---|---|
| Talc | 30 |
| Mica | 35 |
| Titanium oxide | 3 |
| Titanium coated mica | 5.5 |
| Red No. 202 | 0.5 |
| Silicon oxide powder | 3 |
| Sorbitan diisostearate | 1 |
| Squalane | 7 |
| Methyl phenyl polysiloxane | 15 |

<Manufacturing Process>

The pigments were mixed. Other ingredients were added with heating and mixing to the mixture, and were mixed and ground. A pressed-state rouge was obtained by molding the mixture into a medium-sized pan.

Compounding Example 4-17
Liquid Eye Liner

| | |
|---|---|
| Isoparaffin | 58.97 |
| Hydrocarbon resin | 5 |
| Carnauba wax | 1 |
| Candelilla wax | 5 |
| Cholesterol | 2 |
| Ethyl alcohol | 5 |
| Purified water | 8 |
| Organophilic montmorillonite | 3 |
| Black iron oxide | 10 |
| Silicon oxide powder | 1 |
| Sorbitan monostearate | 1 |
| Perfume | 0.03 |

<Manufacturing Process>

An activator, water, organophilic montmorillonite, and the pigment were added to a part of isoparaffin and were mixed and dispersed uniformly. The mixture was maintained at 85° C. The residue of isoparaffin, resin, and wax were added to a pot and dissolved uniformly at 90° C. The dispersion which was prepared in advance was added to the mixture and was dispersed and mixed at 85 to 90° C. Perfume was added to the mixture. The mixture was gradually cooled down to 30° C. An eye liner of water resistance was obtained by filling the mixture to the prescribed container.

Compounding Example 15
Dual Purpose Foundation

| | |
|---|---|
| Titanium oxide processed with silicone | 20 |
| Mica processed with silicone | 22 |
| Iron oxide processed with silicone | 3 |
| Silicon oxide powder | 5 |
| Liquid petrolatum | 4.5 |
| Methyl polysiloxane | 25 |
| Methyl hydrogen polysiloxane | 20 |
| Sorbitan sesquioleate | 0.5 |

<Manufacturing Process>

The pigment part was mixed in uniformly. Then, the oily components and activators were added and mixed with the mixture. After grinding the mixture by an atomizer, the mixture was press-molded to the prescribed medium-sized pan.

As explained in the above, the external preparation for skin which compounds silicon oxide powder has good persistence in the skin and can make the feeling of use favorable.

Micelle Holding Powder

The present inventors paid attention to the micelle that silicon oxide is separated on the outer shell in the case where a rod-like or fine mesoporous powder is prepared. Also though a cationic surfactant which comprises the micelle is removed in the case where the mesoporous powder is prepared, the present inventors studied the micelle holding powder which used a functional material such as a pharmaceutical agent as the cationic surfactant or which was coated silicon on a material which can form the micelle with the cationic surfactant.

Namely, the present inventors studied to form an outer shell with respect to an aggregate of a material to be held and not to form with inserting the material to be held to the carrier which had a pore in later.

As a result of this, the present inventors found that the micelle holding powder in accordance with the present invention had a hexagonal structure as like said mesoporous powder and a function that could gradually release the cationic material which was contained in the pore.

Since a powder in accordance with the present invention formed the outer shell which was composed of silicon around the micelle which was made from the cationic material as the material to be held, an existing amount of the cationic material in the pore was approximate 100% and the powder could always be maintained proper holding state without considering the pore size and molecular size of the cationic material.

Cationic Material

As stated above, a quaternary ammonium salt or a material which can form a micelle together with the quaternary ammonium salt is preferable as the cationic surfactant to be involved in the pore.

In exemplifying the quaternary ammonium salt definitely, an alkyl trimethyl ammonium chloride such as octyl trimethyl ammonium chloride, cetyl trimethyl ammonium chloride, stearyltrimethylammonium chloride, and the like, a dialkyl dimethyl ammonium chloride such as dioctyl dimethyl ammonium chloride and the like and an alkyl dimethyl benzyl ammonium chloride such as octyl dimethyl benzyl ammonium chloride and the like are listed as an alkyl quaternary ammonium salt. Also, as an examples of a cyclic quaternary ammonium salt, an alkyl pyridinium chloride such as cetyl pyridinium chloride and the like and alkyl isoquinorin chloride and the like are listed.

These quaternary ammonium salts are necessary to form a rod-like micelle by adjusting the pH to 10.5 or less in the water solution.

Among these quaternary ammonium salts, benzalkonium chloride, cetyl pyridinium chloride, benzethonium chloride and the like are listed as the quaternary ammonium salt which has an antibacterial activity. A micelle holding powder which has antibacterial activity can be obtained by using these quaternary ammonium salts.

The present invention is further explained by listing a more definite examples of the present invention in the following.

EXAMPLE 5-1

400 g of sodium hydroxide (manufactured by Nacalai Tesque Co., Ltd.) of a guaranteed reagent was dissolved into 1 liter of ion-exchanged water. 300 g of silicon dioxide (#200, manufactured by Aerosil Co. Ltd) which is commercially available was added to the dissolution and was stirred. Sodium silicate ($NaSiO_3$) was obtained by calcining the dispersion for 5 hours at 700° C. 0.5 mol of said sodium silicate and 1 mol of benzalkonium chloride were added to 1 liter of ion-exchanged water and were dissolved at 50° C. The pH value on this occasion was 12.13. Further, 2N-HCl was gradually added to the dissolution and the pH value was adjusted to 8.5. The dissolution was then filtrated and washed with water 5 times repeatedly and a powder which holds benzalkonium chloride was obtained by drying this at room temperature by washing with acetone at room temperature.

COMPARATIVE EXAMPLE 5-1

A micelle holding powder which comprises benzalkonium chloride in the pore was prepared with the same process as Example 5-1. A mesoporous powder that nothing is comprised in the pore was obtained by calcining the obtained powder for 5 hours at 700° C. and by removing the benzalkonium chloride in the pore.

A property of the micelle holding powder of the present invention was studied.

First, the inventors conducted X-ray diffraction with respect to Example 5-1 and Comparative Example 5-1.

A measurement of X-ray diffraction was conducted by using JDX-350 manufactured by JEOL Ltd, at 2 degree (2 θ)/min. CuK α ray was used as an X-ray source. Slit breadth was 1 θ–0.2 mm–1 θ.

Figure 18:
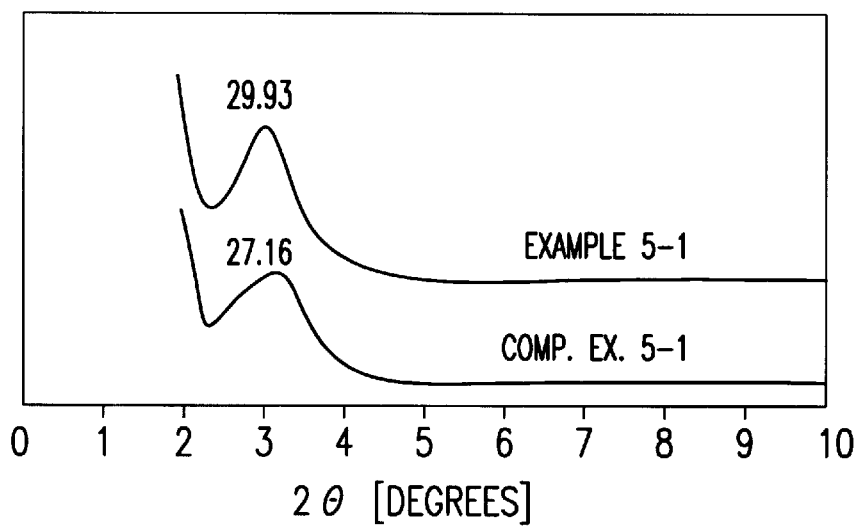
FIG. 18 is an X-ray diffraction diagram of a micelle holding powder in accordance with the present invention and a comparative example.

This results are shown in FIG. 18.

As is clear from the drawing, a micelle holding powder which has a hexagonal structure was manufactured in Example 5-1 as like in Comparative Example 5-1, Consequently, even in the case where the cationic material was left in the pore, it is indicated that a micelle holding structure as like the case that the cationic material was removed, was formed.

Then, the present inventors conducted TG-DTA measurement of Example 5-1 and compared TG-DTA of Example 5-1 with TG-DTA of benzalkonium chloride which was comprised in the pore. The present inventors studied releasing property of benzalkonium chloride in Example 5-1.

Figure 19:
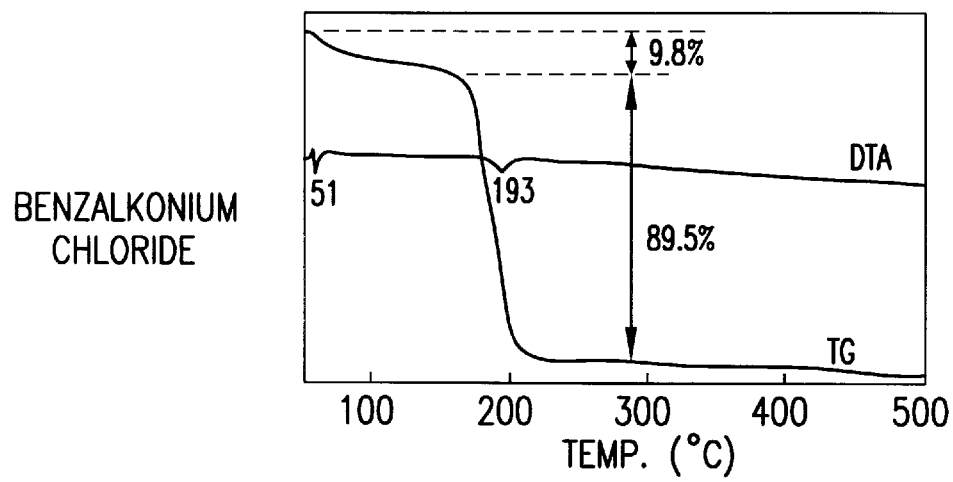
FIG. 19 are an explanatory view showing a result of TG-DTA measurement of benzalkonium chloride and micelle holding powder of Example 5-1.
Figure 19:
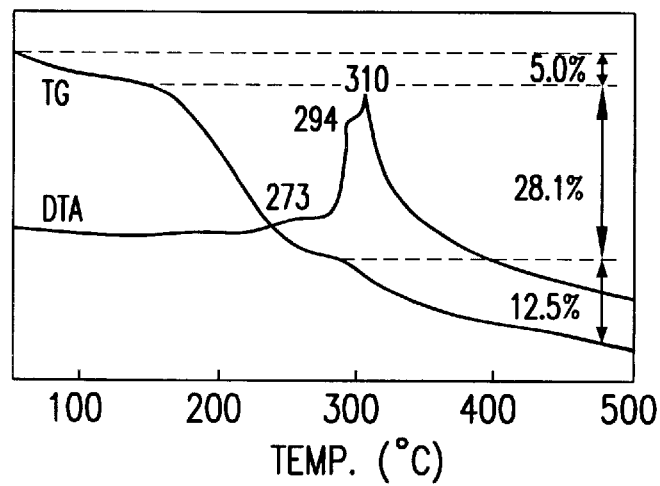
Figure 20A:
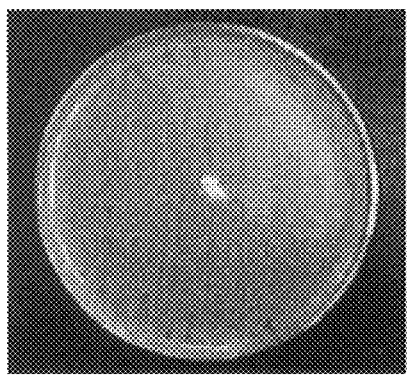
FIG. 20 are an explanatory view showing antibacterial activity of a micelle holding powder which comprises benzalkonium chloride, (a), (b), (c), (d) and (e) shows the case does not comprise benzalkonium chloride, the case comprise stearyltrimethylammonium chloride in the place of benzalkonium chloride, the case comprise benzalkonium chloride, the case comprise benzalkonium chloride and the powder is cultivated at 70° C., and the case that an amount of the powder is increased, respectively.
Figure 20B:
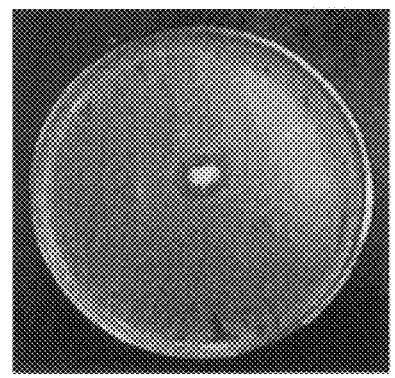
Figure 20C:
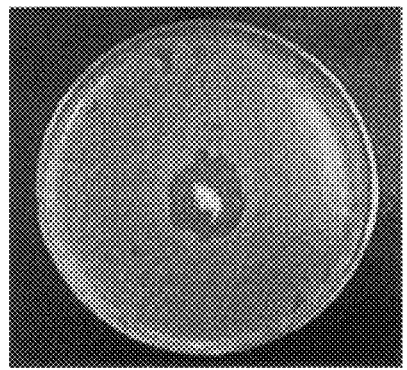
Figure 20D:
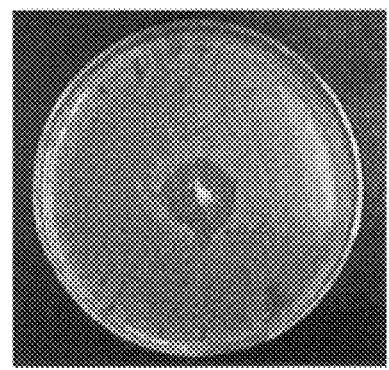
Figure 20E:
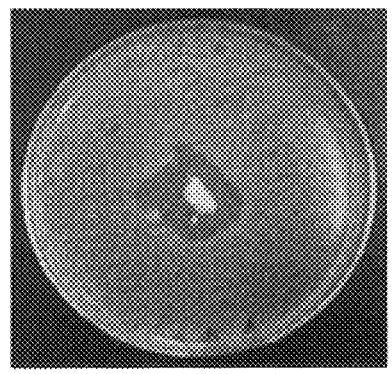

The results are shown in FIG. 19.

As is clear from the drawing, it is thinkable that benzalkonium chloride was decomposed by endothermal reaction, because mass of benzalkonium chloride was suddenly changed in the vicinity of 193° C.

On the contrary, as a result of Example 5-1, mass of the powder was gradually changed. It is indicated that this is the mass change of benzalkonium chloride to be held and benzalkonium chloride was gradually released, because the micelle holding powder which was an outer shell was never decomposed even at higher temperature of 700° C.

Also, it became clear that benzalkonium chloride was held without decomposed even at higher temperature and was gradually released, because mass change was gradually occurred at 150° C.–300° C. in Example 5-1.

The present inventors further conducted a culture test by using Example 5-1, Comparative Example 5-1 and Example 5-2 which was prepared by the following process in order to prove that antibacterial property of benzalkonium chloride could be shown in Example 5-1.

EXAMPLE 5-2

400 g of sodium hydroxide (manufactured by Nacalai Tesque Co., Ltd.) of a guaranteed reagent was dissolved into 1 liter of ion-exchanged water. 300 g of silicon dioxide (#200, manufactured by Aerosil Co. Ltd) which is commercially available was added to the dissolution and was stirred. Sodium silicate ($NaSiO_3$) was obtained by calcining the dispersion for 5 hours at 700° C. 0.5 mol of said sodium silicate and 0.5 mol of stearyl-trimethylammonium chloride were added to 1 liter of ion-exchanged water and were dissolved at 50° C. The pH value on this occasion was 11.8. Further, 2N-HCl was gradually added to the dissolution and the pH value was adjusted to 8.5. The dissolution was then filtrated and washed with water 5 times repeatedly and a powder which holds stearyl-trimethylammonium chloride was obtained by drying this at room temperature by washing with acetone.

As is clear from FIG. 20, a bacterium was bled in a whole part of a petri dish and antibacterial activity was not displayed in Comparative Example 1 which removed benzalkonium chloride by calcination (FIG. 20 (a)). Also, a lack of colony was observed in a part of the periphery of the powder in Example 5-2 which comprised stearyltrimethyl ammoniumchloride which shows antibacterial activity weaker than that of benzalkonium chloride, in the pore (FIG. 20 (b)). Also, a lack of colony which was broader than Example 5-2 was observed in the periphery. of the powder in Example 5-1 which comprised benzalkonium chloride which shows strong antibacterial activity, in the pore (FIG. 20 (c)).

Further, when the inventors conducted a culture test by using the powder of Example 5-1 and by adjusting a culture temperature to 70° C., a lack of colony which was the same with the case that the powder was cultured at room temperature (FIG. 20 (c)) was observed (FIG. 20 (d)). Also, a lack of colony was observed in broader part in the case where an amount of the powder of Example 5-1 was determined with 10 g and was cultured at 70° C. (FIG. 20 (e)). It became clear that strong antibacterial activity was worked.

Therefore, in the case where a micelle holding powder which was manufactured according to the present invention, for example, is compounded to an external preparation for skin such as cosmetic, a functional cosmetic can be obtained by gradually releasing the cationic material which was held such as benzalkonium chloride which has antibacterial activity.

An amount of the micelle holding powder in the case where the micelle holding powder was compounded to the external preparation for skin is at will according to the form of the external preparation for skin. However, the amount of the micelle holding powder is 0.1–80 wt % in general. The compounding amount of the micelle holding powder in case of compounding to an emulsion or dispersion product is 0.1–50 wt % in general. Also, the compounding amount of the micelle holding powder in case of compounding to a powder or pressed-powder product, is 0.1–70 wt % in general.

Further, in addition to the above-mentioned micelle holding powder, the other ingredients which can be generally compounded to an external preparation can compound within the qualitative and quantitative range that the effects of the present invention are not spoiled. For example, humectant, wax, pigment, oily component, surfactant, antiseptic, antioxidant, chelating agent, alkali, water-soluble high polymer, oil-soluble high polymer, clay mineral, and the like can be listed.

A definite compounding examples of the composition of the present invention are explained in the following.

| Compounding Example 5-1 Powdery Foundation | |
|---|---|
| Micelle holding powder of Example 5-1 | 5.0 wt % |
| Talc | 25.0 |
| Mica | 52.95 |
| Yellow iron oxide | 1.0 |
| Red iron oxide | 0.5 |
| Black iron oxide | 0.05 |
| Titanium oxide | 5.0 |
| Liquid petrolatum | 5.0 |
| Lanolin | 5.0 |
| Ethylparaben | 0.3 |
| Perfume | 0.2 |
| Total | 100.0 wt % |

As explained in the above, a micelle holding powder of the present invention has a property such as a pharmaceutical agent comprised in the pore, can improve a heat resistance of the pharmaceutical agent, and gradually release the property of the surfactant. Also, since a silicon containing material in dissolution state is separated on the outer shell of the micelle according to a process for manufacturing the micelle holding powder of the present invention, a homogenous micelle holding powder can be obtained. Further, the particle size of the powder can be adjusted in extremely ease.

Perfume Holding Powder

The present inventors paid attention to the mesoporous powder which mainly composed of silicon oxide and conducted the tests shown in the following.

Namely, 0.5 mol of sodium metasilicate ($Na_2SiO_3$) and 0.1 mol of behenyltrimethylammonium chloride (BTC) were dissolved into 1 liter of ion-exchanged water, The temperature at this time was maintained at 70° C. The pH value of the mixture was adjusted to 8–9 by adding 2N-hydrochloric acid with flow velocity of 120 ml/min just after the dissolution. Then, the dissolution was filtrated and washed with water. A rod-like mesoporous powder was obtained by calcining the dissolution for 3 hours at 700° C.

A perfume holder of linalool (perfume) was formed by using this rod-like mesoporous powder and β-cyclodextrin (β-CD).

These holders were left on a constant-temperature bath of 40° C. Linalool concentration at a head-space portion was measured by GC-MAS.

Figure 21:
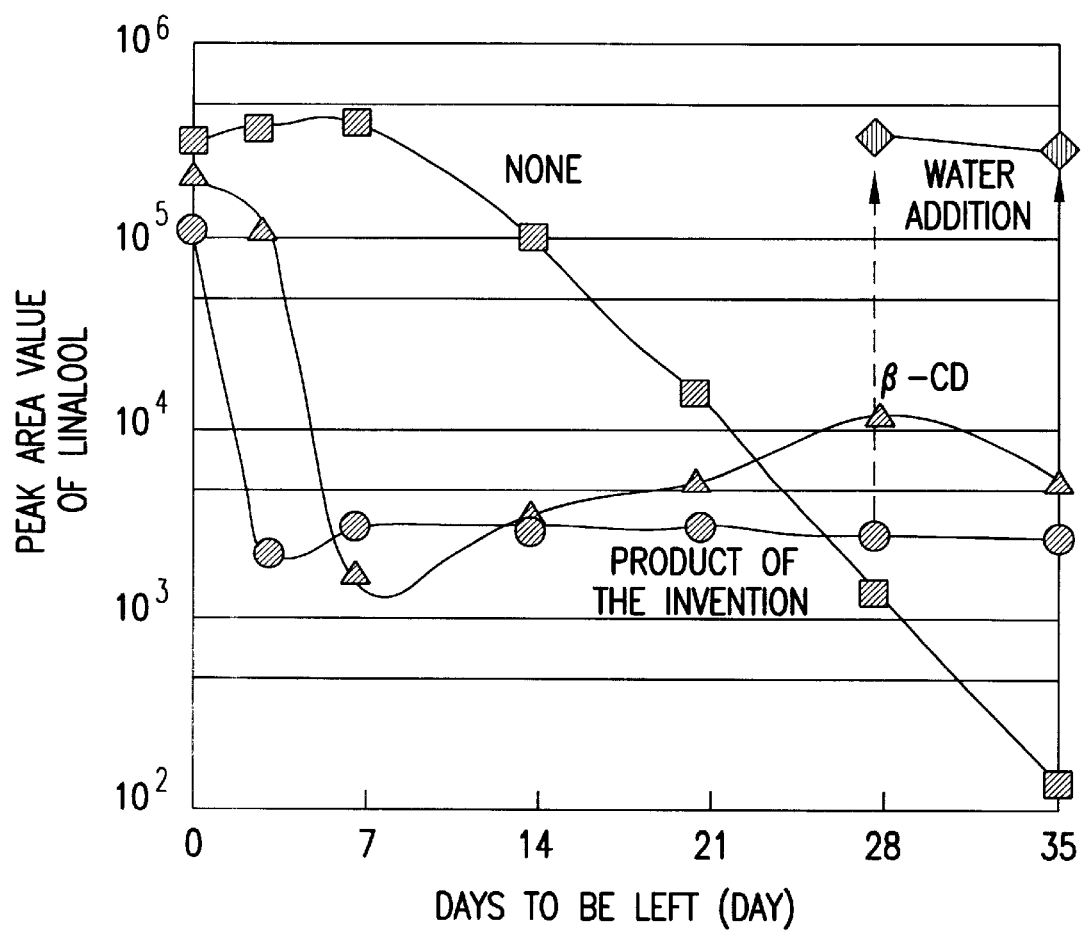
FIG. 21 is an explanatory view of a perfume holding effect by a perfume holding powder in accordance with the present invention.

The results are shown in FIG. 21. Linalool concentration was shown by peak area value.

As is clear from the drawing, the concentration of the holder was rapidly decreased with the passage of the number of the days to be left in the case where a simple linalool was used. On the contrary, the concentration of the holder became minimum after 1 hour from the leaving in the case where β-CD was used as a carrier. Then, the concentration of the holder was gradually increased to about 1 month later. The concentration of the holder was decreased when the time has further passed. It is thinkable that this change of the concentration is influenced by not so much the change of the volatile velocity as the decomposition or denaturation of β-CD.

However, the concentration of the holder was reached to a steady state about 3 days and was almost not changed after that, in the case where the rod-like mesoporous powder in accordance with the present invention was used as a carrier.

The further notable thing is that the concentration of perfume in the head-space was rapidly increased, i.e., volatile velocity was changed, in the case where water was added to the perfume holding powder in accordance with the present invention. Though the cause of this are unknown in some part, it is thinkable as explained in the following. A mesopore of the mesoporous powder used in the present invention has a uniform pore size. A contact area between the perfume and outside air was approximate consistent with the mesopore area despite increase and decrease of perfume and a volatile velocity became constant in the case where perfume was held in the mesopore. Further, in the case where water was injected to the perfume holding powder, the perfume was forced out the external part of the mesopore by substituting perfume and water because hydrophilic property in mesopore was relative high.

Next, the present inventors prepared a deodorant powder as shown in TABLE 10 and studied the effects of the perfume holding powder in accordance with the present invention. Each deodorant powder was prepared so as that the concentration of the perfume might be 1% with respect to the composition.

TABLE 10

| | Test Ex. 6-1 | Test Ex. 6-2 | Test Ex. 6-3 | Test Ex. 6-4 |
|---|---|---|---|---|
| Perfume | | | | |
| Perfume holding powder | 5.0 | | | |
| Perfume holding silica gel | | 5.0 | | |
| Perfume holding cyclodextrin | | | 5.0 | |
| Simple perfume | | | | 1.0 |
| Normal powder | | | | |
| Aluminium chlorohydrate | 5.0 | 5.0 | 5.0 | 5.0 |
| Zinc oxide | 5.0 | 5.0 | 5.0 | 5.0 |
| Talc | 80.0 | 80.0 | 80.0 | 84.0 |

TABLE 10-continued

|  | Test Ex. 6-1 | Test Ex. 6-2 | Test Ex. 6-3 | Test Ex. 6-4 |
|---|---|---|---|---|
| Oily component | | | | |
| Liquid petrolatum | 5.0 | 5.0 | 5.0 | 5.0 |
| Effects | | | | |
| Smell of product (After 3 days) | + | ++ | ++ | +++ |
| Smell of product (After 1 month) | + | + | ++ | + |
| Smell in use (After 1 month) | +++ | + | ++ | + |

In manufacturing the various test examples, each powder was contained in a Henschel mixer and was stirred uniformly. The residuary ingredients were then added and mixed uniformly. The deodorant powder was obtained by grinding the mixture by an atomizer and compression-molding at a container.

Also, these powders were preserved under room temperature and open.

As is clear from the result shown above, though smell of the product was not so much strong and maintained faint smell condition, the powder was exhibited considerable strong fragrance by substituting with perspiration or sebum on the skin at the time of use, according to a deodorant powder which uses the perfume holding powder in accordance with the present invention.

Further, according to the deodorant powder in accordance with the present invention, the powder has an absorption function of sebum and favorably controlled stickiness after use.

Next, the present inventors studied the relation between the ratio of the mesoporous powder and the perfume and the effects thereof.

TABLE 11

| Comp. Examples | 6-5 | 6-6 | 6-7 | 6-8 | 6-9 | 6-10 | 6-11 | 6-12 | 6-13 |
|---|---|---|---|---|---|---|---|---|---|
| Mesoporous powder | 0.01 | 0.1 | 0.5 | 1.0 | 5.0 | 10.0 | 30.0 | 50.0 | 80.0 |
| Perfume | 1.0 | 1.0 | 1.0 | 1.0 | 1.0 | 1.0 | 1.0 | 1.0 | 1.0 |
| Normal powder | | | | | | | | | |
| Aluminium chlorohydrate | 5.0 | 5.0 | 5.0 | 5.0 | 5.0 | 5.0 | 5.0 | 5.0 | 5.0 |
| Zinc oxide | 5.0 | 5.0 | 5.0 | 5.0 | 5.0 | 5.0 | 5.0 | 5.0 | 5.0 |
| Talc | Bal. | Bal. | Bal. | Bal. | Bal. | Bal. | Bal. | Bal. | Bal. |
| Oily component | | | | | | | | | |
| Liquid petrolatum | 5.0 | 5.0 | 5.0 | 5.0 | 5.0 | 5.0 | 5.0 | 5.0 | 5.0 |
| Smell | | | | | | | | | |
| Right after production | ++ | ++ | ++ | + | + | + | + | + | + |
| After 1 month | + | + | + | + | + | + | + | + | + |
| Using time | ++ | ++ | +++ | +++ | +++ | +++ | +++ | ++ | ++ |

As is clear from TABLE 11, in the case where 0.01–0.1 part by weight of the mesoporous powder was added with respect to 1 part by weight of the perfume, powdering could be possible in sufficient. However, volatilization of the perfume in preservation was easy to proceed and smell at the time of use, (though within the range of practical use) became slightly weak. Also, smell tended to be slightly weak, since the extent of the pore became too high in the case where 30 parts by weight or more of the mesoporous powder was compounded.

Accordingly, it is preferable that a mixing ratio of the perfume and the mesoporous powder is about 1:0.5–1:30 at weight ratio.

Also, a mesoporous powder used in the present invention has an effect for protection of cosmetic spoiling, since the mesoporous powder has a superb oil absorption property and water absorption property.

Various materials can be held in the present invention. For example, in the case where a drug for oral administration is held in the powder, the drug can be released in mouth or stomach after administration. In order to manufacture the perfume holding powder of the present invention, it is only to mix and knead the various liquid or liquefaction materials. Also, it is preferable to conduct a hydrophobic or hydrophilic treatment to the surface of the mesoporous powder according to the types of the material to be held or the system that the perfume holding powder to be compounded.

What is claimed is:

1. A non-laminar silicon oxide powder which is mainly composed of silicon oxide and has almost homogenous pores, wherein the powder is a mesoporous powder having a pore depth of 50–300 nm, and
   wherein the powder is in the form of rod-shaped mesoporous powder particles having an outer diameter of 20–200 nm and a mesopore which is elongated to its longer direction.

2. A non-laminar silicon oxide powder according to claim 1, wherein a primary particle unit is formed by aggregating two or more rod-shaped mesoporous powder particles in network state.

3. A non-laminar silicon oxide powder which is mainly composed of silicon oxide having an outer diameter of 20–200 nm and lacking mesopores and wherein a shape of the powder particle is rod-shaped and nonporous.

4. A non-laminar silicon oxide powder according to claim 3, wherein a primary particle unit is formed by aggregating two or more of rod-shaped non-porous powder particles in network state.

5. A process for manufacturing a non-laminar silicon oxide powder which is mainly composed of silicon oxide and has almost homogenous pores, said process comprising:
   a solubilization step wherein a silicate at a concentration of 0.1–5 M is dissolved in the presence of a cationic surfactant at a pH adjusted to 11 or more, and wherein the proportions of $SiO_2$ and $Y_2O$ (Y is an alkali metal atom) in said silicate are in the range of $0<SiO_2/Y_2O<2$;

a condensation step wherein the pH is adjusted to 10.5 or less, a rod-shaped micelle is formed with said cationic surfactant and said silicate is condensed on said micelle and wherein said silicate forms thereby an outer shell of said micelle; and a removal step wherein said cationic surfactant is removed from said micelle.

6. A process for manufacturing a rod-shaped mesoporous powder which is mainly composed of silicon oxide and has almost homogenous pores wherein the powder has a pore depth of 50–300 nm, said process comprising:

a solubilization step wherein a silicate at a concentration of 0.3–1.2 M is dissolved in the presence of a cationic surfactant at a pH adjusted to 11 or more, and wherein the proportions of $SiO_2$ and $Y_2O$ (Y is an alkali metal atom) in said silicate are in the range of $0<SiO_2/Y_2O<2$;

a condensation step wherein the pH is adjusted to 10.5 or less within 30 minutes, a rod-like micelle is formed with said cationic surfactant and said silicate is condensed on said micelle and wherein said silicate forms thereby an outer shell of said micelle; and a removal step wherein said cationic surfactant is removed from said micelle.

7. A process for manufacturing a rod-shaped non-porous powder which comprises, a solubilization step wherein a silicate at a concentration of 1.2–2.0 M is dissolved in the presence of a cationic surfactant at a pH of 11 or more, and wherein the proportions of $SiO_2$ and $Y_2O$ (Y is an alkali metal atom) in said silicate are in the range of $0<SiO_2/Y_2O<2$;

a condensation step wherein the pH is adjusted to 10.5 or less within 30 minutes, a rod-like micelle is formed with said cationic surfactant and said silicate is condensed on said micelle and wherein said silicate forms thereby an outer shell of said micelle; and a removal step wherein said cationic surfactant is removed from said micelle.

8. A process for manufacturing a non-laminar silicon oxide powder as in claim 5, wherein said silicate is mainly composed of $Na_2SiO_3$.

9. A process for manufacturing a non-laminar silicon oxide powder as in claim 5, wherein said cationic surfactant is a quaternary ammonium salt.

10. A process for manufacturing a non-laminar silicon oxide powder according to claim 9, wherein quaternary ammonium salt: silicate is 1:1–1:50 at molar ratio.

11. A process for manufacturing a non-laminar silicon oxide powder according to claim 10, wherein quaternary ammonium salt: silicate is 1:3–1:20 at molar ratio.

12. A process for manufacturing a non-laminar silicon oxide powder as in claim 9, wherein said quaternary ammonium salt has an alkyl group having a carbon number of 18 or more.

13. A process for manufacturing a non-laminar silicon oxide powder as in claim 9, wherein said quaternary ammonium salt has an alkyl group having a carbon number less than 18 and coexist with 0.1–3M of a salt of an acid excluding silicon.

14. A cosmetic preparation comprising a non-laminar silicon oxide powder of claim 2.

15. A micelle holding powder comprising silicon oxide placed on a micelle outer shell in the presence of a cationic material which has a surface active ability.

16. A micelle holding powder according to claim 15, wherein said cationic material which forms micelle is a quaternary ammonium salt.

17. A micelle holding powder according to claim 16, wherein said quaternary ammonium salt which forms micelle has antibacterial activity.

18. A process for manufacturing a micelle holding powder which comprises, a solubilization step wherein a silicate is dissolved in the presence of a cationic surfactant at a pH of 11 or more, and wherein the proportions of $SiO_2$ and $Y_2O$ (Y is alkali metal atom) in said silicate are in the range of $0<SiO_2/Y_2O<2$; and a condensation step wherein the pH is adjusted to 10.5 or less, a rod-shaped micelle is made of said cationic surfactant and a silicate is condensed on said rod-like micelle.

19. A perfume holding powder in which perfume is held to the non-laminar silicon oxide powder of claim 1.

20. A process for manufacturing a rod-shaped mesoporous powder as in claim 6, wherein said silicate is mainly composed of $Na_2SiO_3$.

21. A process for manufacturing a rod-shaped mesoporous powder as in claim 6, wherein said cationic surfactant is a quaternary ammonium salt.

22. A process for manufacturing a rod-shaped mesoporous powder according to claim 21, wherein quaternary ammonium salt:silicate is 1:1–1:50 at molar ratio.

23. A process for manufacturing a rod-shaped mesoporous powder according to claim 22, wherein quaternary ammonium salt:silicate is 1:1–1:20 at molar ratio.

24. A process for manufacturing a rod-shaped mesoporous powder as in claim 21, wherein said quaternary ammonium salt has an alkyl group having a carbon number of 18 or more.

25. A process for manufacturing a rod-shaped mesoporous powder as in claim 21, wherein said quaternary ammonium salt has an alkyl group having a carbon number less than 18 and coexist with 0.1–3M of a salt of an acid excluding silicon.

26. A cosmetic preparation comprising the non-laminar silicon oxide powder of claim 1.

27. A perfume holding powder in which perfume is held to the non-laminar silicon oxide powder of claim 2.

28. A cosmetic preparation comprising a non-laminar silicon oxide powder of claim 3.

29. The process of claim 7, wherein said rod-like non-porous powder is mainly composed of silicon oxide having an outer diameter of 20–200 nm and is lacking in mesopores.

* * * * *

UNITED STATES PATENT AND TRADEMARK OFFICE
CERTIFICATE OF CORRECTION

PATENT NO.   : 6,511,668 B1  
DATED        : January 28, 2003  
INVENTOR(S)  : Shoichiro Shio and Asa Kimura It is certified that error appears in the above-identified patent and that said Letters Patent is hereby corrected as shown below:

<u>Title page,</u>
After Item [76], inventors, insert -- [73] Assignee:  Shiseido Co., Ltd., Tokyo (JP) --

Signed and Sealed this

Twenty-ninth Day of July, 2003

JAMES E. ROGAN
*Director of the United States Patent and Trademark Office*